United States Patent [19]

Silver et al.

[11] Patent Number: 5,171,273
[45] Date of Patent: Dec. 15, 1992

[54] SYNTHETIC COLLAGEN ORTHOPAEDIC STRUCTURES SUCH AS GRAFTS, TENDONS AND OTHER STRUCTURES

[75] Inventors: Frederick H. Silver, Bangor, Pa.; Yasushi P. Kato, Edison, N.J.

[73] Assignee: University of Medicine and Dentistry of New Jersey, Newark, N.J.

[21] Appl. No.: 297,115

[22] Filed: Jan. 13, 1989

[51] Int. Cl.$^5$ .......................... A61F 2/28; A61F 2/10; A61F 2/02

[52] U.S. Cl. ...................................... 623/13; 623/66; 623/16

[58] Field of Search .................. 623/1, 10, 11, 12, 16, 623/66

[56] References Cited

U.S. PATENT DOCUMENTS

| | | | |
|---|---|---|---|
| 3,551,560 | 12/1970 | Thiele | 623/11 |
| 4,420,339 | 12/1983 | Kato | 623/66 |
| 4,544,516 | 10/1985 | Hughes et al. | 264/108 |
| 4,629,458 | 12/1989 | Pinchuk | 623/1 |
| 4,642,117 | 2/1987 | Nguyen et al. | 623/16 |
| 4,772,288 | 9/1988 | Borner et al. | 623/1 |
| 4,801,299 | 1/1989 | Brendel et al. | 623/66 |
| 4,846,835 | 7/1989 | Grande | 623/16 |
| 4,880,429 | 11/1989 | Stone | 623/16 |
| 4,911,710 | 3/1990 | Milthorpe | 623/66 |

OTHER PUBLICATIONS

Academic Press, NY, 1, 211-213, (1979) Harkness, Mechanical Properties of Connective Tissues in Relation to Function.
Amer J. Sports Med., 8, 1:1-8 (1979), Kennedy et et al. Intraarticular Replacement of the Anterior Crucitate, etc.
Amer. J. Sports Med., 13, 4:242-247 (1985) Rodkey et al. A Partially Biodegradable Material Device for Repair and etc.
Archives of Biochemistry and Biophysics, 235 1:178-85 (1984) Collagen Fibrillogensis in vitro:Comparison of Types I, II, III.
Biochemistry, 20, 2325-30 (1981) Kleinman et al. Interaction of Fibronectin with Collagen Fibrils.
Biocem. Biophys, Acta, 670, 362-69 (1981) Birk et al. Corneal and Scleral Collagen Fiber Formation in vitro.
Biochem. J., 23, 1-14 (1986) Poole, Health and Disease:-Structure and Functions.
Biochem. J., 109, 857-66 (1968) Toole et al. Effect of Chondrotin Sulfate-Protein on the Formation of Collagen etc.
Biochem. J., 127, 607-08 (1972) Lowther et al. The Influence of Glycoprotein on Collagen Fibril Formation in the Presence etc.
Biochem. J., 233, 587-97 (1984) Vogel et al. Specific Inhibition of Type I and II Collagen Fibrillogensis by the Small etc.
Biomat., 7, 3-8 (1986) Doillon et al. Collagen-Based Wound Dressing, Effects of Hyaluronic Acid and Fibronectin on Wound Healing.
Biomats., in press (2988) Kato et al. Mechanical Properties of Collagen Fibers.
Clin. Orthop., 196, 196-01 (1985) McMaster Histologic Xenograft Assessment of Canine Anterior Cruciate Substitution with Bovine.
Clin. Orthop. 196, 9-14 (1985) Freidman et al. Autogenic Anterior Cruciate Ligament (ACL) Anterior Reconstruction of the Knee.
Col. Res. Rel. 3, 393-05 (1983) Silver et al. Kinetic Analysis of Collagen Fibrillogensis.
Col. Res. Rel. 5, 481-92 (1985) Doillon et al. Collagen Fiber Formation in Repair Issue.
Connective Tissue Research 12, 59-70 (1983) Dunn et al. Viscoelastic Behavior of Human Connective Tissues.

(List continued on next page.)

Primary Examiner—David J. Isabella
Attorney, Agent, or Firm—Weiser & Stapler

[57] ABSTRACT

The invention provides graft, prothesis, orthopaedic structures, implants and like body replacement parts which are constituted of synthetic collagen fibers, an embodiment of which is a tendon or a ligament prosthesis, graft or implants. These body parts have a combination of very useful properties, particularly high tensile strength combined with biocompatability.

18 Claims, 22 Drawing Sheets

OTHER PUBLICATIONS—Continued

COOR, 196 51-60 (1985) Mendes et al Histologic Patern of Biomechanic Properties of the Carbon Fiber-Augmented Ligament Tendon.

COOR, 196, 196-201 (1985) McMaster Histologic Assessment of Canine Anterior Cruciate of the Carbon Fiber-Augmented Ligament Tendon.

Int. J. Biol. 7, 135-40 (1985) Brokaw et al. Turbidimetric and Morphological Studies of Type I Collagen Fiber Self Assembly in vitro . . . etc.

Int. J. Biol., 8, 177-82 (1986) Berg et al. Physical Characterization of Type I Procollagen in Solution: Evidence that the Propeptides . . . etc.

J. Amer. Leather Chem. Assoc., 70, 146-58 (1985) Hughes al. A Oriented Fibrillar Collagen and its Application to Biomedical Devices.

J. Biomed. Mater. Res., 10, 259-71 (1976) McMaster et al. Tendon Grafting with Gluraraldehyde Fixed Material.

J. Bone Joint Sur. 59-B, 53-7 (1977) Jenkins et al. Induction of Tendon Formation by Carbon Implants.

Methods of Enzymology, 8, 52-55 (1966) Davidson Analysis of Sugars Found in Mucopolysaccharides.

NYU Press, Ch. 1,6&7, (1987) Silver Biological Materials, Structure Properties and Modelling Soft Tissues.

SEM, 2, 897-03, (1985) Doillon et al. Collagen Deposition During Wound Repair.

SEM 3, 1313-20 (1984) Doillon et al. Fibroblast-Collagen Fibers in vitro and in vitro.

The Journal of Biological Chem. 255, 9427-33 (1980) Silver Type I Collagen Fibrillogensis in vitro.

The Journal of Biological Chem. 256, 4973-77 (1981) Silver Type I Collagen Fibrillogenis in vitro.

The Journal of Investigative Dermatology, 84, 1:9-13 (1985) Dunn et al. Mechanical Analysis of Hypertrophic Scar Tissue, Structural . . . etc.

FIG. I

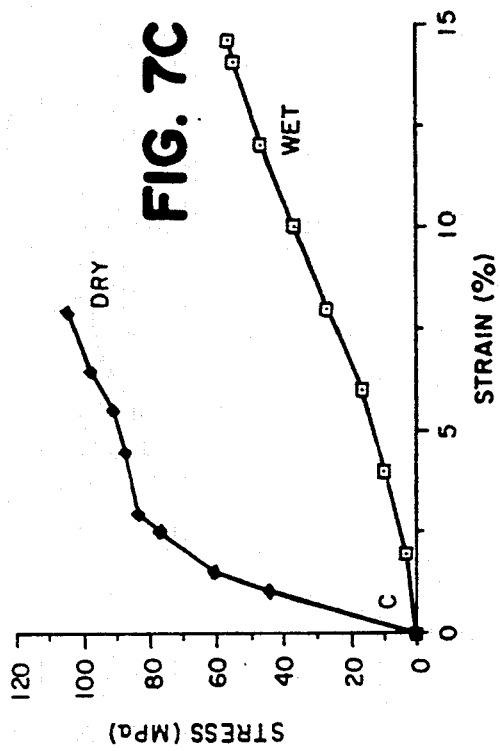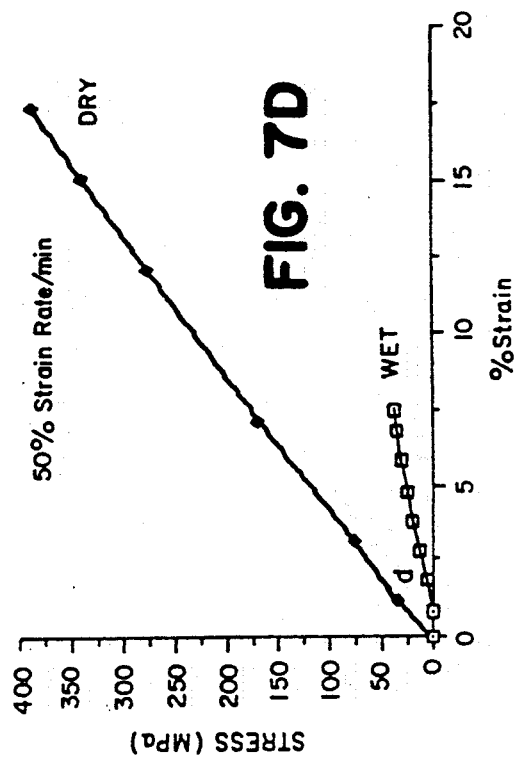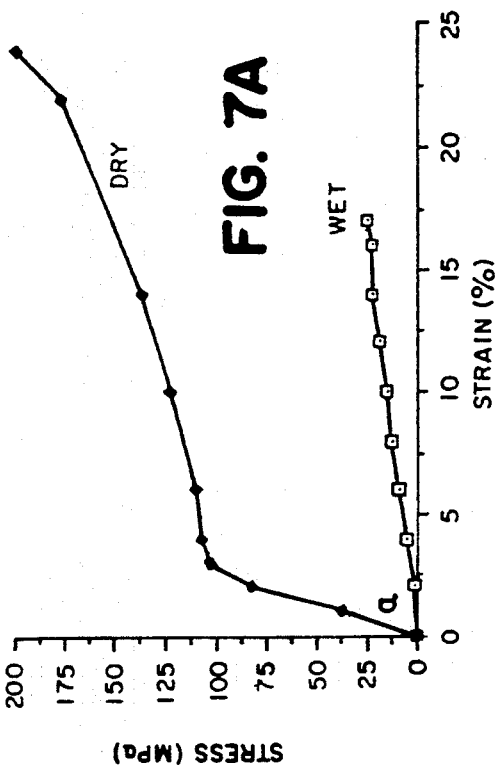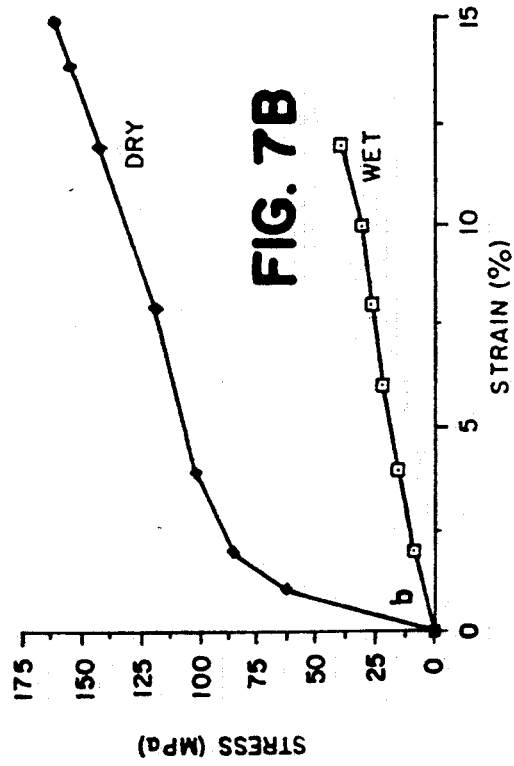

| SAMPLE | n | STRAIN RATE/MIN(%) | UTS ± SD (MPa) | US ± SD (%) | E ± SD (MPa) |
|---|---|---|---|---|---|
| RTT (W) | 8 | 10 | 39.0 ± 11.10 | 8.10 ± 1.700 | 570 ± 84.9 |
|  | 10 | 50 | 34.9 ± 14.40 | 7.10 ± 1.200 | 552 ± 172.3 |
|  | 10 | 100 | 32.6 ± 12.00 | 6.70 ± 3.10 | 478 ± 129.9 |
| RTT (D) | 9 | 10 | 366 ± 79.3 | 13.80 ± 2.90 | 2690 ± 421 |
|  | 9 | 50 | 366 ± 87.5 | 15.60 ± 3.70 | 2130 ± 548 |
|  | 9 | 100 | 363 ± 99.2 | 14.50 ± 3.30 | 2250 ± 523 |

UTS, ULTIMATE TENSILE STRESS; US, ULTIMATE STRAIN; E, MODULUS TANGENT TO STRESS-STRAIN CURVE; RTT, RAT TAIL TENDON FIBER; W, WET; D, DRY; SD, STANDARD DEVIATION; n, NUMBER OF SAMPLES.

FIG. 8

| SAMPLE | n | STRAIN RATE/MIN (%) | UTS SD (MPa) | US SD (%) | E1 SD (MPa) | E2 SD (MPa) |
|---|---|---|---|---|---|---|
| DHT3 ± C1 (W) | 15 | 10 | 27.4 ± 5.60 | 17.50 ± 4.40 | 179.5 ± 54.7 | - |
|  | 12 | 50 | 23.9 ± 3.80 | 14.70 ± 2.10 | 198.1 ± 56.7 | - |
|  | 10 | 100 | 31.3 ± 4.70 | 17.70 ± 2.20 | 170.1 ± 32.9 | - |
| DHT3 C1 (D) | 5 | 10 | 168.8 ± 39.5 | 19.50 ± 5.80 | 4320 ± 1440 | 574 ± 204 |
|  | 5 | 50 | 184.2 ± 22.4 | 21.0 ± 4.80 | 3600 ± 785 | 569 ± 345 |
|  | 5 | 100 | 177.6 ± 32.1 | 22.2 ± 3.90 | 3910 ± 1205 | 544 ± 271 |

UTS, ULTIMATE TENSILE STRESS: US, ULTIMATE STRAIN: DHT3 + C1.3 d SEVERE DEHYDROTHERMAL TREATMENT FOLLOWED BY 1d EXPOSURE TO CYANAMIDE VAPOR: W, WET: D, DRY: SD, STANDARD DEVIATION: n, NUMBER OF SAMPLES: E1, LOW STRAIN MODULUS: E2, UPPER STRAIN MODULUS.

FIG. 9

| SAMPLE | n | STRAIN RATE/MIN(%) | UTS SD(MPa) | US SD(%) | E1 SD(MPa) | E2 SD (MPa) |
|---|---|---|---|---|---|---|
| GLUT 2 | 10 | 10 | 66.2 ± 17.20 | 16.10 ± 2.70 | 407 ± 96.6 | - |
|  | 13 | 50 | 59.2 ± 17.90 | 13.80 ± 2.90 | 503 ± 127.7 | - |
|  | 12 | 100 | 50.0 ± 17.40 | 14.90 ± 3.50 | 412 ± 83.4 | - |
| GLUT 2 | 5 | 10 | 180.7 ± 27.6 | 15.30 ± 2.10 | 3820 ± 376 | 788 ± 231 |
|  | 5 | 50 | 152.0 ± 43.6 | 14.80 ± 1.800 | 4070 ± 401 | 764 ± 157.6 |
|  | 5 | 100 | 149.9 ± 45.0 | 12.80 ± 3.20 | 3240 ± 539 | 567 ± 195.7 |

UTS, ULTIMATE TENSILE STRESS; US, ULTIMATE STRAIN: GLUT2, GLUTARALDEHYDE 2d VAPOUR; W, WET; D, DRY; SD, STANDARD DEVIATION; n, NUMBER OF SAMPLES; E1, LOW STRAIN MODULUS; E2, UPPER STRAIN MODULUS.

FIG. 10

| SAMPLE | n | STRAIN RATE/MIN(%) | UTS SD(MPa) | US SD(%) | E1 SD(MPa) | E2 SD (MPa) |
|---|---|---|---|---|---|---|
| GLUT 4 | 12 | 10 | 64.2 ± 15.0 | 15.10 ± 2.70 | 456.5 ± 82.7 | - |
|  | 12 | 50 | 55.5 ± 11.80 | 14.40 ± 3.60 | 403 ± 82.7 | - |
|  | 13 | 100 | 51.8 ± 13.00 | 13.60 ± 3.40 | 384 ± 57.5 | - |
| GLUT 4 | 5 | 10 | 139.4 ± 47.0 | 14.60 ± 1.700 | 3070 ± 647 | 529 ± 242 |
|  | 5 | 50 | 142.4 ± 38.0 | 11.80 ± 4.70 | 3550 ± 311 | 578 ± 216 |
|  | 5 | 100 | 144.4 ± 26.6 | 12.60 ± 2.50 | 4860 ± 1238 | 803 ± 444 |

UTS, ULTIMATE TENSILE STRESS; US, ULTIMATE STRAIN; GLUT 4, GLUTARALDEHYDE 4d VAPOUR; W, WET; D, DRY; SD, STANDARD DEVIATION; n, NUMBER OF SAMPLES; E1, LOW STRAIN MODULUS; E2, UPPER STRAIN MODULUS.

FIG. 11

BIREFRINGENCE RETARDATION MEASUREMENTS ON CROSSLINKED FIBERS CONTAINING DERMATAN SULFATE. NUMBER IN PARENTHESIS INDICATES THE NUMBER OF SAMPLES IN EACH SET.

| % W/V OF DERMATAN SULFATE (GAG) ADDED TO FIBER | DIAMETER OF DRY FIBER $\times 10^{-3}$ nm | BIREFRINGENCE RETARDATION/THICKNESS $\times 10^3$ |
|---|---|---|
| 0.001 | 61.6 ± 3.42 (20) | 0.67 ± 0.13 (20) |
| 0.005 | 67.5 ± 2.38 (20) | 0.51 ± 0.21 (20) |
| 0.010 | 65.4 ± 1.46 (20) | 0.75 ± 0.06 (20) |

FIG. 19

BIREFRINGENCE RETARDATION MEASUREMENTS ON CROSSLINKED FIBERS CONTAINING CHONDROITIN SULFATE. NUMBERS IN PARENTHESIS INDICATE THE NUMBER OF SAMPLES IN THE SET.

| % W/V OF CHRODROITIN SULFATE (GAG) ADDED TO FIBER | DIAMETER OF DRY FIBER $\times 10^{-3}$ nm | BIREFRINGENCE RETARDATION/THICKNESS $\times 10^3$ |
|---|---|---|
| 0.001 | 50.0 ± 1.18 (20) | 0.80 ± 0.14 (20) |
| 0.005 | 55.4 ± 1.27 (20) | 0.82 ± 0.12 (20) |
| 0.010 | 60.0 ± 2.38 (20) | 0.87 ± 0.21 (20) |

FIG. 20

BIREFRINGENCE RETARDATION MEASUREMENTS ON CROSSLINKED
FIBERS CONTAINING DEXTRAN SULFATE. NUMBER IN PARENTHESIS IN-
DICATES THE NUMBER OF SAMPLES IN EACH SET.

| % W/V OF DEXTRAN SULFATE ADDED TO FIBER | DIAMETER OF DRY FIBER $\times 10^{-3}$ nm | BIREFRINGENCE RETARDATION/THICKNESS $\times 10^3$ |
|---|---|---|
| 0.001 | 50.0 ± 1.13 (10) | 1.43 ± 0.21 (10) |
| 0.005 | 60.0 ± 3.34 (10) | 1.11 ± 0.27 (10) |
| 0.010 | 60.0 ± 1.12 (10) | 0.94 ± 0.06 (10) |

FIG. 21

BIREFRINGENCE RETARDATION MEASUREMENTS ON CROSSLINKED FIBERS CONTAINING HIGH MOLECULAR WEIGHT PROTEOGLYCAN (PG1) AND CHONDROITIN SULFATE PROTEOGLYCAN (CS-PG). NUMBER IN PARENTHESIS INDICATES THE NUMBER OF SAMPLES IN EACH SET.

| TYPE OF FIBER | DIAMETER OF DRY FIBER, T $\times 10^{-3}$ nm | BIREFRINGENCE RETARDATION/THICKNESS $\times 10^3$ |
|---|---|---|
| PG1 | 49.2 ± 1.39 (10) | 1.2 ± 0.13 (10) |
| CS-PG | 50.0 ± 1.50 (10) | 1.2 ± 0.25 (10) |

FIG. 22

VOLUME FRACTION OF COLLAGEN IN RECONSTITUTED COLLAGEN FIBERS

| | |
|---|---|
| CONTROL | 0.95 ± 2% |
| PG I | 0.97 ± 2% |
| CS-PG | 0.98 ± 2% |
| CS-GAG | 0.98 ± 2% |
| DS-GAG | 0.98 ± 2% |
| DEXS | 0.97 ± 2% |

FIG. 23

TABLE 4 STRAIN, MODULUS AND ULTIMATE TENSILE STRENGTH OF RECONSTITUTED COLLAGEN TYPE I FIBERS

NUMBER IN PARENTHESIS INDICATES THE NUMBER OF SAMPLES IN EACH SET.

| TYPE OF FIBER | % STRAIN AT BREAK | MODULUS (MPa) | UTS (MPa) |
|---|---|---|---|
| CONTROL (1% w/v COLLAGEN TYPE I) | 14.6 ± 1.32 (40) | 432 ± 62.3 (40) | 58.1 ± 7.32 (40) |
| 1% w/v COLLAGEN TYPE I + 0.01g/100ml CS (PG) | 12.4 ± 3.34 (20) | 141.0 ± 34.9 (20)* | 7.4 ± 1.52 (20)* |
| 1% w/v COLLAGEN TYPE I + 0.01g/100ml PG I | 15.1 ± 2.38 (23) | 621.0 ± 75.1 (23)* | 90.4 ± 21.4 (23)* |

* SIGNIFICANTLY DIFFERENT THAN CONTROL AT 0.99 CONFIDENCE LEVEL

FIG. 24

%W/W OF GAGS AND PGS IN RECONSTITUTED COLLAGEN FIBERS

| TYPE OF FIBER | % W/W OF MACROMOLECULE ADDED TO THE BATH | % W/W OF MACROMOLECULE ATTACHED TO EACH FIBER |
|---|---|---|
| CONTROL | 0.00 | 0.00 ± 0.02 |
| DS-GAG | 0.01 | 0.89 ± 0.22 |
| CS-GAG | 0.01 | 0.54 ± 0.09 |
| PGI-PG | 0.01 | 0.43 ± 0.01 |
| CS-PG | 0.01 | 0.36 ± 0.10 |

FIG. 25

SYNTHETIC COLLAGEN ORTHOPAEDIC STRUCTURES SUCH AS GRAFTS, TENDONS AND OTHER STRUCTURES

BACKGROUND OF THE INVENTION

This invention relates to high strength reconstituted collagen fibers which are particularly well suited as grafts for orthopaedic, dermal, cardiovascular, and dental implants, prosthesis and other applications particularly in human subjects.

Collagen fibres are the structural elements that give shape to mammalian tissues as well as acting as the scaffold over which cells migrate and deposit new connective tissue. Types I, II and III collagen fibres in the form of cross-linked networks prevent over-expansion of the aorta and heart, limit shear deformation of cartilage and biaxial tensile stretching of skin and transmit tensile loads in tendons. Type I collagen fibers make up the connective tissue in various body parts of mammals like in tendons, skin, bone and fascia. The location and tissue source of different collagens are explained in Reference No. 82 which is incorporated herein by reference.

In the description which follows reference is made to publications identified by numerals in parenthesis, which are more fully cited towards the end of the description and which publications are all included herein by references. Also other publications are listed which are of background interest.

Currently no synthetic material is available to satisfactorily replace the function of normal tendon or ligament indefinitely. No biodegradable or polymeric synthetic tendon or ligament is available which provides mechanical properties equivalent to an autograft or which induces repair by tissue ingrowth. Such a material would be valuable in tendon or ligament reconstruction as a substitute for autograft material. Synthetic polymers developed for tendon or ligament replacement utilize permanent fiber bundles or monofilaments designed to directly bear load for the life of the implant. These implants can fail as a result of fatigue and require surgical removal of graft remnants.

Implants which encourage neotendon formation have also been developed. However, none have proven to stimulate collagenous ingrowth with mechanical characteristics resembling normal tendon.

Several approaches have been tested to replace the function of tendons and ligaments damaged as a result of athletic injury. Replacement of tendon and ligament has been achieved using biodegradable and non-biodegradable synthetic polymers and biological tissues from the knee. But these also have short comings as yet unsolved.

Non-porous polymeric implants have a limited fatigue life and ultimately fail when used to replace the function of a ligament such as the anterior cruciate. Implanted tows of polymeric and carbon fibers result in the controlled formation of a "neo-tendon" through the deposition of aligned collagen. Biological structures such as glutaraldehyde-fixed bovine tendon and autogenous tendons and ligaments elongate after surgical implantation and eventually do not support loads in the knee.

These methods all require a lengthy rehabilitation period. These prior art techniques are well described in background literature in references 9, 10, 11, 14, 15 and 17.

Autologous tendon transfers now provide the only long term solution to traumatic tendon or ligament loss. This is reported in literature references 1, 2, 3 and 9. There are however, serious drawbacks to the use of autogenous tissues. Autograft materials or autologous transfers are not readily available; also they cause loss of normal functioning of the structure and a slow rate of incorporation and maturation of repair tissue. Further, the extensive use of autologous tissue is potentially disabling and disfiguring to the individual.

This description shows how unsatisfactory autologous materials are in repair or replacement of tendons, ligaments, etc.

From the description of the prior art it is evident that a serious and urgent need exists for high strength fibrous materials suitable for use as a graft that is long lasting and has biocompatibility with a host, which graft has the desired properties.

The graft of the invention overcome many of the prior art difficulties and problems and have a combination of advantageous properties non-existance in the prior art. The collagenous graft used of the invention can be manufactured without sacrifice of the host's tissue. The graft of the invention quickly incorporates the repair tissue which is a needed characteristic in the design of biomaterials that enhance the deposition of repair tissue in skin, tendon and the cardiovascular system. Although high-strength oriented and unoriented collagenous materials are reported in the literature (22) no report is known of collagen fibers of small diameter that can be processed into woven and non-woven textile prostheses which have the necessary properties that simulate or exceed those of the natural body part.

In this description of the invention, the following terms have the following meaning:

"Autograft" means transferring a tissue or organ by grafting into a new position in the body of the same individual.

"Implant" means a graft which is woven into and secured in the surrounding tissue.

"Graft" means anything inserted into something else, or contacted upon something else so as to become an integral or associated part of the latter and it includes materials and substances which are either added to an already intact structure or serve as a replacement substitute or repair to a damaged or incomplete structure. Thus a "graft" is intended to be given the broadest possible meaning and encompasses a prothesis, implant or any body part substitute for any mammal (animal or human).

The invention provides collagen grafts for numerous applications particularly where high tensile strength and biocompatability are essential. It is evident that both of these properties are essential for grafts. If tensile strength is not high enough or of limited duration, there is the real risk that the graft would rupture (or weaken). Thus, physical integrity is essential. Biocompatability is also necessary otherwise rejection of the graft could occur. The invention also provides collagen proteoglycan fibrous grafts which have even greater tensile strength than the non-proteoglycan grafts of the invention. These are especially well suited for specialized applications where such property is particularly important. The invention further provides a method for making improved collagen proteoglycan fibers for use in such grafts.

The invention provides further implants in which the collagen grafts are woven and secured into the surrounding tissue. The surrounding tissue then invades the graft material. The graft is revascularized and eventually replaced by the host's tissues.

The invention further provides for grafts with physical properties that can be manipulated or processed into a variety of shapes, thicknesses, stiffnesses in woven or non-woven forms.

Other embodiments provided by the invention will become apparent from the description which follows.

The invention contributes to fulfilling a serious need in the medical, bio-medical, cosmetic, body-repair, body reconstruction and related arts.

SUMMARY OF THE INVENTION

The invention has several embodiments. In one of its embodiments the invention provides a high strength synthetic collagen graft constituted of high strength reconstituted crosslinked collagen fibers embedded into a loose uncrosslinked collagen matrix. The synthetic collagen graft is useful to repair damaged tendons and ligaments. The graft is also useful as vascular and cardiovascular tubes or to strengthen and stiffen abdominal and muscular wounds or holes. The collagen grafts of the invention are also useful in the repair of dermal, dental, cardiovascular, and orthopaedic structures as well as a topical application or a drug delivery matrix. The grafts of the invention help stimulate neo-tendon or repair tissue formation by incorporating repair tissue rapidly. The grafts provides structural support for the rapid ingrowth of new connective tissue. The surrounding tissue invades the graft material with fibroblasts, capillaries, and connective tissue. Eventually the graft is replaced by the host's invading tissue.

The grafts use synthetic collagen fibers of hitherto unattained small diameter, high tensile strength, durability and elasticity. These grafts process physical properties which permit them to be processed into varying shapes, sizes, thicknesses and stiffnesses. The grafts can be processed into woven and non-woven materials.

The grafts of the invention are biologically compatible with a host. They simulate the morphological and biomechanical characteristics of the host's natural tissue.

In one embodiment of the invention high molecular weight chondroitin sulfate proteoglycan in added during the latter stages of collagen fiber synthesis to be incorporated into interfibrillar spaces and as a result enhances the ultimate tensile strength of the collagen fibers formed.

Accordingly it is an object of the invention to make a high strength collagen graft that is useful as an implant for the repair of damaged tendon and ligaments or other body parts. Specifically, it is an object of the invention to provide a collagen prosthesis or implant comprising collagen fibers of small diameter (e.g., less than about 60 microns), high tensile strength, varying elasticity and an open mesh structure that can be processed into woven and non-woven structures.

It is a further object of this invention to provide a material for ligament, tendon muscular, orthopaedic, dermal, dental or cardiovascular repair with the morphological and bio-mechanical characteristics of the naturally occurring tissue.

It is a further object of the invention to provide a scaffold for aligned collagen deposition with normal mechanical and histologic appearance and for cellular invasion by autogenous grafts.

Furthermore, it is an object of the invention to provide implants which are capable of promoting regeneration of neotendon or repair tissue at a more rapid rate than that provided by implantation of autograft.

It is also an object of the invention to shorten the period of implant protection or the period during which the neotendon repair tissue needs to be protected until it can assume its function. Thus it is an object of the invention to shorten the period until the tendon or other body structure regains sufficiently functional tensile strength.

It is also an object of the invention to provide a synthetic collagen graft prosthesis or implant of small diameter that can be processed into woven and non-woven textile prosthesis and that can assume a variety of elasticities and degrees of stiffness.

It is a further object of the invention to provide for reconstituted collagen fibers of high strength and small diameter that enhance the deposition of repair tissue in skin, tendon, ligament, muscle, bone, orthopaedic and cardiovascular structures.

Accordingly, the invention provides in one of its important embodiment a man-made (as opposed to natural) body part or graft which has or simulates the biomechanical features of the natural body parts, which (gradually after insertion or implementation) becomes an integral part of the body. A specific embodiment of the grafts of the invention, is a tendon or a ligament which implanted into a test animal has all the necessary biocompatability and mechanical strength, elasticity and other properties of a natural tendon or ligament and further promotes healing by attracting fibroblasts into the fibrous structure of the graft.

The collagen structures of the invention are useful to support organs in mammals, like stomach, heart, blood vessels and tissue planar structures. Meshed structures of the invention are useful to support the stomach wall externally in situations were the skins and/or muscles are injured.

Patches and tubes of the materials of the invention (woven or knitted materials) are useful to support areas of the heart and blood vessel walls that are damaged as by disese. Woven and non-woven materials can be used to cover areas that are injured by burns, or to augment or contour tissue for cosmetic reconstruction of skin in the face or other body areas.

It is evident that the collagen orthopaedic structures of the maintain are ideally suited for important uses in biomedical and orthopaedic reconstruction of the human body which may open up a new area related to the improvement of human health.

Other objects of the invention will become apparent to one of average skill in the art to which the invention pertains.

BRIEF DESCRIPTION OF THE DRAWINGS

FIG. 7 shows Typical tensile stess-strain curves for collagen fibers cross-linked: (a) for 3d using the dehydrothermal technique and for 1d cyanamide vapour (DHT3+Cl); (b) for 2d in glutaraldehyde vaopur (Glut 2); and (c) for 4d in glutaraldehyde vapour (Glut 4). For comparision the curve for rat tail tendon fibers is shown (d).

FIG. 8 shows Table of mechanical properties of wet and dry rat tail tendon fibers (2 cm gauge length).

FIG. 9 shows Table of mechanical properties of reconstituted collagen fibers cross-linked using DHT3+c! vapour (2 cm gauge length).

FIG. 10 shows Table of mechanical properties of reconstituted collagen fibers cross-linked for 2d using glutaraldehyde vapour (2 cm gauge length).

FIG. 11 shows Table of mechanical properties of reconstituted collagen fiber cross-linked for 4d using glutaraldehyde vapour (2 cm length).

FIG. 19 shows birefringence retardation measurements on crosslinked fibers containing dermatan sulfate. Number in parthesis indicates the number of samples in each set.

FIG. 20 shows birefringence retardation measurements on crosslinked fibers containing chondroitin sulfate. Numbers in parenthesis indicate the number of samples in the set.

FIG. 21 shows birefringence retardation measurements on crosslinked fibers containing dextran sulfate. Numbers in parenthesis indicates the number of samples in each set.

FIG. 22 shows birefringence retardation measurements on crosslinked fibers containing high molecular weight proteoglycan (PGl) and chondroitin sulfate proteoglycan (CS-PG). Number in parenthesis indicates the number of samples in each set.

FIG. 23 shows volume fraction of collagen in reconstituted collagen fibers.

FIG. 24 shows strain, modulus and ultimate tensile strength of reconstituted collagen type I fibers. Number in parenthesis indicates the number of samples in each set.

FIG. 25 shows Percent % W/W and PGs in reconstituted collagen fibers.

DETAILED DESCRIPTION OF THE INVENTION

Figure 1:
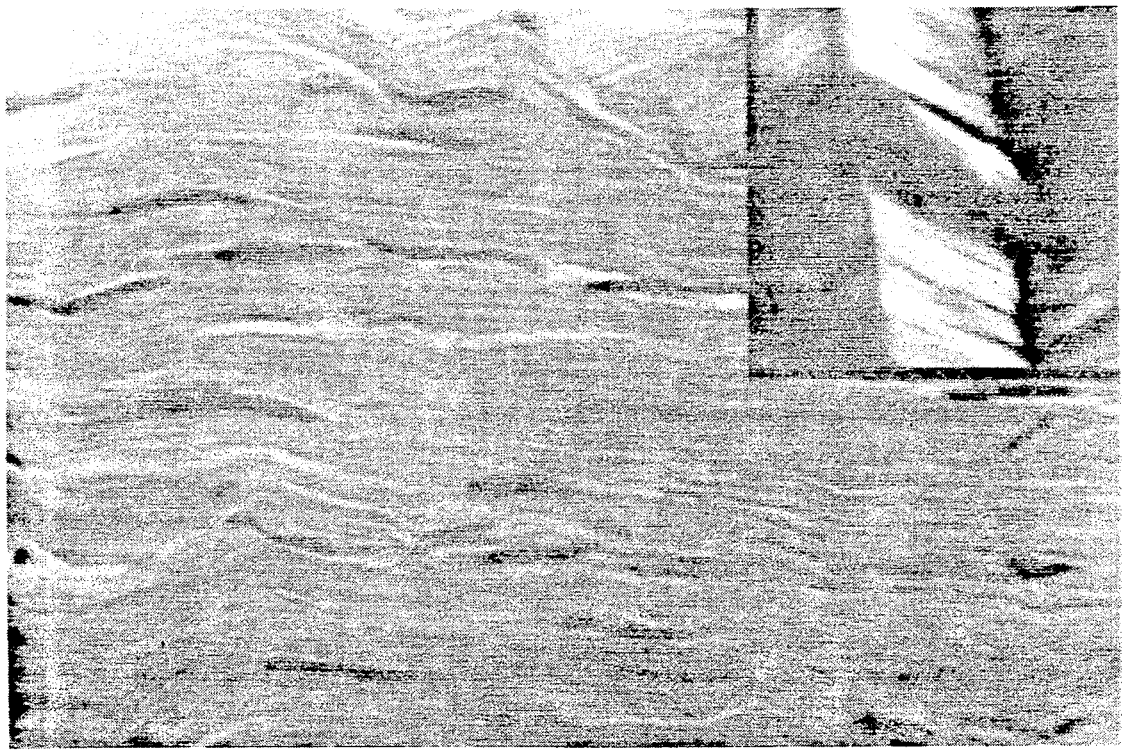
FIG. 1 shows the appearance of autograft tendon at 20 weeks after implantation (magnification 40×). Note fibroblast and vascular invasion with minimal inflammation. Residual autograft is seen interfaced with new invading tissue. The upper right corner demonstrates by poliarized microscopy that crimp has been maintained (magnification 10×).

The graft of the invention have numerous applications which can assume different physical embodiments or different geometrical shapes.

The synthetic collagen graft material of the invention are useful as a mesh, sheet, film, tube, circular casing, filament, fiber or as a woven or non-woven fabric. The graft material is useful as a general prosthesis or implant, specifically as a tendon or ligament prothesis or implant. The graft of the invention is useful in numerous applications like vascular grafts, skin substitutes, tendon and ligament for hernia repair for wound healing, bone repair structures in matrices with various pharmacological agents as well as other similar or related uses. The synthetic collagen graft material of the invention can be used as cardiovascular or vascular tubes. It can be used to strengthen or stiffen abdominal wounds or any muscular wound. The graft material useful as a covering for the brain or as a tube for nerve regeneration.

The graft material comprises collagen fibers with a diameter around the range of about 20–60 microns. Collagen fibers with a diameter of less than about 20 microns generally do not have the requisite mechanical strength for use in the hereinabove listed applications as a graft, implant or prosthesis. Collagen fibers with diameters greater than about 60 microns generally do not have the requisite malleability and ease of manipulation. Thus, the invention encompasses collagen fiber materials that are considered drapable and non-drapable in the textile sense.

The collagen fibers used in the grafts of the invention have tensile strengths in the range of about 30 to about 91 MPa. It is a noteworthy aspect of the invention that the fibers of the invention can have ultimate tensile strengths exceeding that of autograft materials or naturally occurring tendon fibers in laboratory animals. The collagen materials of the invention can have an index of refraction in the range of about 1.4 to about 1.7, generally about 1.6.

In accordance with the invention, the synthetic collagen graft material of the invention is generally implanted into surrounding tissue of the subject. The graft is secured to the surrounding tissue with sutures, biodegradable fasteners or appropriate other means. The collagenous graft promotes healing of damaged or missing muscle, tendon, ligament, orthopaedic, denture dermal or vascular structure by supporting and providing a scaffold for the migration of fibroblasts into the fibrous structure of the graft. The graft promotes incorporation of repair tissue into the implanted graft while supporting the maturing repair tissue. The implant graft is eventually replaced by newcollagenous tissue. The graft material is biodegradable with the host's naturally produced repair tissue supplanting the graft material. Furthermore, the graft is biologically morphologically and bio-mechanically compatible with surrounding tissue of the subject treated.

The collagen graft material of the invention can also be used in various topical applications. Such applications include uses as a wound dressing or as a drug delivery matrix system. In such use the pharmacological agent is released slowly as the graft material is replaced by the host body's natural collagen tissue the wide variety of pharamological agents can be employed with this technique.

The use of the collagen graft material of this invention as a tendon 1 ligament prothesis or implant can be described as follows. A gastrocnemius tendon of an animal (in this case a rabbit), is totally removed from mature New Zealand white rabbits. In its place a synthetic collagen fibrous tendon of the invention was woven into the musculotendinous junction proximately and distally looped around the calcaneus between the bone and plantar fascia. Both end of the implanted tendon secured with sutures and the normal length of the tendon restored. Similarly the gastrocnemius tendon excised from the centralateral leg of the same rabbit and reanastomized. This centralateral leg served as an autograft central. The wounds were closed and sterile dressing were applied. The rabbit ambulated without restriction and no animal became infected on either the control or implanted side.

At removal all implants and autografts were in continuity with the gastrocnemius and calcaneus. Three weeks after the surgery the implants using the graft material of the invention were invaded by abundant fibroblasts and invading capillaries. By contrast the autograft implant exhibited slower revascularization and no live cells centrally at 3 weeks. The mechanical properties of all the implanted materials returned toward those of fresh tendon in all materials over time. At 20 weeks the ultimate tensile strengths of the implants using the graft material of the invention were either similar to or exceeded the ultimate tensile strengths of the autograft.

Thus the graft material exhibited a tensile strength greater than that of autograft in rabbits. As further described below in Example II the graft material also exhibited tensile strength greater than the naturally occurring tendon fiber in rat tail. Further details of the method and results of using graft material of the invention as prothetic implant tendon are described below.

In accordance with the invention, the collagenous fibrous material or collagen fibers which are useful to make the articles of the invention are prepared and used as follows.

Insoluble type I collagen was dispersed in an acidic solution and then extruded through an appropriate tubular means to the desired diameter.

The extruded fibers are soaked in a warm aqueous fiber formation buffer for a sufficient period of time at an appropriate temperature and after rinsing they are air-dried. Specifically in one embodiment the collagen fibers are prepared as follows.

Insoluble type I collagen is obtained from corium. The collagen composition is characterized by dosium decyl sulfate polyacrylamide gel electrophoresis as typical of components of type I collagen.

A dispersion of type I collagen is dilute HCL at a pH 2.0 is prepared. This collagen dispersion is extruded through polyethylene tubing with an inner diameter of 0.28 mm into a 37° C. bath of aqueous fiber formation buffer. In one embodiment the aqueous fiber formation buffer is prepared from 135 mM NaCl, 30 mM TES (N-Tris(hydroxylmethyl) methyl -2- aminoethane sulphonic acid) and 30 mM sodium phosphate dibasic. The final bath pH is adjusted to about 7.5. Chemically similar or equivalent compounds may also be used as well as other collagen fiber formation buffers well known in the art. After immersion in the fiber formation buffer for 45 minutes, the fibers are placed in isopropanol for at least four hours. The fibers are then rinsed in distilled water and air dried under tension.

The formation of collagen fibers is described elsewhere in Goldstein eta al, Development of a Collagen Synthetic Implant (1988) which is incorporated herein. Further details are given in Examples I, II and III below.

The collagen fibers are then cross-linked using glutaraldehyde or a combination of severe dehydration and treatment with cyanamide. Various cross-linking techniques can be employed but not limited to the following crosslinking reagents and treatments: glutaraldehyde, dehydration and exposure to cyanamide treatment, carbodimide or sucrimimidyl active ester, ribose, polysaccharide and other sugars and amino-thiols.

U.S. Pat. No. 4,703,108 to Silver et al which discloses numerous cross-linking techniques is incorporated herein by reference.

Further details as to the method of cross-linking are also give in Examples I and II.

In another embodiment of the invention proteoglycans are associated with the collagen fibers of the invention. For that purpose the extruded fibers are immersed in a fiber formation buffer containing the proteoglycan. The fibers are soaked for a sufficient time at an appropriate temperature to cause the proteoglycan to be incorporated into the fibrous structure. For instance, the fibers can be soaked for 60 minutes at 37° C. The fibers are then rinsed with appropriate liquids to remove excess glycan and dried. Soaking temperature can be in the range from about 15° C. to 50° or 60° C. with either longer or shorter soaking periods, as may be desirable.

Specifically this embodiment of the invention is prepared as follows. Proteoglycans in a concentration between 0.01 and 0.02 g/100 ml were added to the fiber formation buffer and stirred. A 1% w/v collagen dispersion was placed in a syringe to which polyethylene tubing of internal diameter 0.58 mm was attached. Fibers were extruded into a fiber formation buffer. The fiber formation buffer is composed of 135 mM NaCl, 30 mM TES (N-tris(hydroxylmethyl) methyl -2-aminoethane sulphonic acid) and 30 mM sodium phosphate dibasic. The final pH is adjusted to about the neutral range such in the range of about 6.5 to 7.5. Chemically similar or equivalent compounds may also be used as well as other collagen fiber formation buffers well know in the art. The extruded fibers were left in the tray containing fiber formation buffer for 60 minutes. The buffer was maintained at 37° C. The buffer was removed and replaced by isopropanol. The fibers soaked in isopropanol overnight and were then soaked in distilled water for 15 minutes. The fibers were then removed from the distilled water and air dried under tension. The extruded collagen fibers were then crosslinked by exposure to glutaraldehyde. Fibers which were formed in the presence of high molecular weight proteoglycan were found to have significantly increased ultimate tensile strengths compared to low molecular weight, chondroitin sulfate, glycosaminoglycans or controls. Furthermore collagen fibers formed in the presence of high molecular weight proteoglycans exhibit higher tensile strength than collagen fibers that are crosslinked. Further details are given in Example III below.

The role of proteoglycans in connective tissues is discussed in Harkness, R. D., *Mechanical Properties of Connective Tissues in Relation to Function*, Fibrous Proteins, volume 1, edited by D. A. D., Parry and L. K. Creamer, Academic Press, NY, p. 207-213 (1979) which is incorporated herein by reference. The proteoglycan molecule attaches to the collagen fibrils and imparts strength to the collagen fibers.

Thus, in accordance with the invention, the process for making proteoglycan modified collagen fibers comprises making collagen fibers by extrusion through extrusion means, subjecting the fibers to exposure to a selected proteoglycan in a suitable medium, desirably in an aqueous buffered medium, causing the incorporation of the high molecular weight proteoglycans into the fibrous structure, removing excess proteoglycan and collecting the modified fibers. If desired a cross-linking of the treated fibers can then also be performed. The resulting modified fibers have uniformed properties, especially improved tensile strength.

The high molecular weight proteoglycans which are generally preferred in the invention are large proteoglycan with a core protein with a molecular weight greater than about 100,000 and glycosaminoylycans chain with a molecular weight greater than about 5,000.

In particular the high molecular weight aggregate forming proteoglycan from tendon, aorta, and cartilage that aggregate in the presence of hyaluronic acid and link protein to form proteoglycan aggregates can be used to form the graft. Additionally, small non-aggregating proteoglycans from bone is useful. In particular the high molecular weight proteoglycans from articular cartilage in particularly desirable hereinafter known as "articular cartilage proteoglycan". These proteoglycan generally have a molecular weight of the range of about 1,000,000 to about 3,000,000 typically about 1,200,000. Other proteoglycans desirable for use in the invention include large proteoglycans from tendon with chondroitin sulfate chains of average molecular weight of 17,000 and a core protein molecular weight of 200,000. It is not unlikely that other proteoglycans will also be useful in the invention providing they impart the desirable properties to the collagen fibers, in particular the desired tensile strength.

Other proteoglycans which in accordance with the invention are not as desirable for the purpose of the invention, included dermatan sulfate proteoglycan and chondroitin sulfate proteoglycan from hypertrophic scar tissue. Dermatan sulfate proteoglycan from scar has a molecular weight of about 30,000. Chondroitin sulfate proteoglycan from scar has a molecular weight of about 78,000-80,000.

In general proteoglycan are macromolecules constituted of a protein backbone to which glycosaminoglycan chains and N - and/or 0 - linked oligosaccharides are covalently attached. A hyalurmic acid binding region is located at the N- terminus. The region constitutes approximately one-third to one-fourth of the protein backbone or core. Proteoglycan then can bind specifically to hyaluronic acid and form macromolecular aggregates. These aggregates are organized between collagen fibrils with which hyaluronic acid interacts. A link protein binds to the hyaluronic acid binding region and to hyaluronic acid which leads to molecular shape changes. Similar molecular shape changes occur when the hyaluronic acid binding region binds to hyaluronic acid. The hyaluronic acid binding region is in the form of a folded polypeptide chain with N - linked oligosaccharides evenly distributed on the outside. Little is known about the rest of the core protein. The composition of the glycosaminoglycans chains of proteoglycans, their linkage to core protein, the structures of some proteoglycans and their known or suspected functions are more fully described in Poole, Proteoglycans in Health and Disease Structures and Functions, *Biochemistry Journal,* (1986) 236, 1-14 which is incorporated herein by reference.

The high molecular weight proteoglycan from articular cartilage is the desired form of proteoglycan for use in this invention as presently seen. The high molecular weight proteoglycan from articular cartliage utilized in the invention contains chondrodin sulfate and keratan sulfate side chains. These chains bind to the core protein. Aggregated cartilage proteoglycans contain a high charge density. This permits these molecules to associate with counter ions and water molecules. When confined in a collagenous framework as in the fibers of the invention the bound water or swelling pressure imports rigidity and mechanical strength to the whole fibrous structure or collagenous matrix. The high strength fiber form the constituent parts of the grafts of the invention.

Once the high strength collagen fibers which constitute the graft material of the invention are formed in accordance with the various embodiments of the invention the fibers are collected. The collected fibers are shaped, pressed or formed into sheets, tubes and numerous other shapes of varying dimensions and thickness as desired for the particular application. The fibers can be processed into woven materials. They can be packed with various pharmacologically active agents. These structures then can be directly used as the graft, prosthesis or implant of the invention depending on the need and how the particular structure has been prepared. The fibrous graft can be woven or secured to surrounding tissue as an implant or graft or topically applied and topically secured.

One skilled in the art will shape the structure to the desired application.

The following examples are exemplary of the various embodiments of the present invention discussed herinabove. They are not to be construed as limiting but as illustrative of the process and products of the present invention.

Variations in technique of the type known in the art and understood by those of ordinary skill to be functional equivalents of those disclosed herein may be substituted as desired, for convenience or for optimization of yield, or to simplify or improve the cost-effectiveness of the overall procedure. Therefore, numerous modifications and variations of the present invention are possible which are within the scope of the appended claims.

EXAMPLE I

Materials & Methods

Collagen fibers were prepared from insoluble type I collagen derived from bovine corium. The collagen composition was characterized by sodium decyl sulfate polyacrylamide gel electrophoresis as alpha (a1(1) and a2(1)), beta gamma and higher molecular weight components of type I collagen. Amino acid analysis was consistent with the composition of type I collagen as previously described (21).

Collagen fibers were prepared from a 1% (w/v) dispersion of type I collagen in dilute HCL, pH 2.0. This collagen dispersion were extruded through polyethylene tubing with an inner diameter of 0.28 mm into a 37° C. bath of aqueous sodium phosphate fiber formation buffer as described elsewhere (10). After immersion of 45 minutes, the fibers were placed in isopropanol for at least four hours. They were then rinsed in distilled water for 15 minutes and allowed to air dry under tension overnight. Fibers were placed in a sealed dessicator containing 10 ml of a 25%(w/v) glutaraldehyde solution at room temperature and allowed to vapor crosslinked for 24 hours. These fibers are referred to as Glu-1 below. Alternatively, collagen fibers were placed in an oven at 110° C. in a vacuum of between 50 and 100 m torr for 72 hours. These fibers were then placed in a sealed dessicator containing 20 g of cyanamid in 5 ml of distilled water for 24 hours. These fibers are referred to as DHT3-Cl.

Prostheses containing 200 to 250 individual collagen fibers crosslinked by DHT3-Cl or Glu-1 methods were coated with a 1%(w/v) collagen dispersion in HCL, pH 2.0, air dried overnight and then extensively washed in distilled water. One ml Alcide ® activator and one ml Alcide ® base were added to 10 ml of distilled water and after 10 minutes diluted with 24 ml of phosphate buffer solution. Each implant was immersed in this cold sterilant for at least four hours, and then soaked in one liter of sterile physiological saline prior to implantation.

Protheses of the invention can have as many collagen fibers as may be needed to form the structure needed. Because of the higher tensile strength of the fibers used in the invention, a greater versatility in the size, composition and uses of the graft is made available by the invention.

Surgical Model

Mature New Zealand white rabbits weighing 6–7 lbs were anesthetized with a Xylazine-ketamine cocktail and maintained on Forane-Nitrous oxygen anesthesia.

Exposure of the achilles tendon from the musculotendinous junction to the plantar fascia below the calcaneus was carried out through a lateral curving incision. The using gastrocnemius tendon was totally removed and immediately tested using an Instron (model 1122). In its place, a synthetic tendon of DHT3-Cl or Glu-1 was woven into the musculotaneous junction proximally and distally looped around the calcaneas between the bone and plantar fascia. Both ends of the implant were then secured with horizontal mattress sutures of 4-0 dexon. Normal length was restored. No attempt was made to reproduce in vivo tendon strength with an equivalent implant. The contralateral leg served as an autograft control. Here an identical exposure was carried out and the tendon was excised from both ends, released from all surrounding tissue, and reanastomosed with a modified Kessler repair at both ends. Both wounds were closed with subcutaneous dexon and running nylon for skin and sterile dressings were applied. No immobilzation was provided. For both DHT3-Cl and Glu-1 implants, 5–8 animals were implanted for each of 3, 10, and 20 weeks intervals.

Mechanical and Histologic Analysis

The initial mechanical properties of each implant were determined by tensile testing on an Instron (model 1122) prior to implantation. At sacrifice, both control and synthetic tendons were removed from each animal and kept moist with buffered saline. Tendons were immediately tested using uniaxial tension by clamping the tissue in felt-lined pneumatic grips of an Instron Model 1122. Mechanical tests were done on the material not the graft host junction. Cross-sectional area was measured with a micrometer in two perpendicular planes and calculated as an ellipse. A one centimeter gauge length and 100% per minute strain rate were utilized. Elongation was halted at the point of mechanical failure. Histologic assessment on the same tissue was performed after formalin fixation, paraffin embedding and H & E and trichrome staining. Slides were qualitatively evaluated for infiltration of fibroblasts, inflammatory cells and organization of the neotendon. Contralateral autograft tendons on each animal served as a reference for synthetic implant mechanical properties and histology. Mechanical data was compiled for synthetic tendons and matched allografts at all time intervals. Results were normalized by dividing the mechanical property of the explant by the same property prior to implantation for both autografts and implants. In this manner all measurements were normalized to the time zero data. Statistical analysis by paired student t-test was carried out between all groups.

Results

The rabbits ambulated without restriction and no animal became infected on either the control or implant side. At removal, all implants and allografts were in continuity with the gastrocnemius and calcaneus. The gross appearance of implants and autograft were more like normal tendon at successive time intervals.

Histology

Autograft Implant

Autograft material showed a slow revascularization with no live cells centrally at 3 weeks. By 10 weeks cellular and vascular invasion from the surrounding tissue has begun. Fibroblast celluarity was maximal at 20 weeks, and collagen crimp was maintained at all times (FIG. 1).

Glu-1 Implants

Figure 2:
FIG. 2 shows the appearance of Glu-1 implant 20 weeks post implantation (magnification 10×). Note unorganized fibrous tissue ingrowth between implant fibers. Fibers are still intact. There is no crimp noted in the upper right corner by polarized microscopy (magnification 10×).

By 3 weeks the implants were microscopically invaded by neovascular tissue with abundant fibroblasts and invading capillaries. Glu-1 fibers remained visibly unchanged through all time periods. By 10 weeks, the Glu-1 implant has changed little with increasing inflammatory cells surrounding the implant and minimal reorganization of neovascular tissue. A thin fibrous capsule formed around the implant. This persisted at 20 weeks with little reorganization of the interspersed collagen ingrowth. Polarized light microscopy failed to demonstrate crimp in the ingrowth tissue (FIG. 2).

DHT3-Cl Implants

Figure 3:
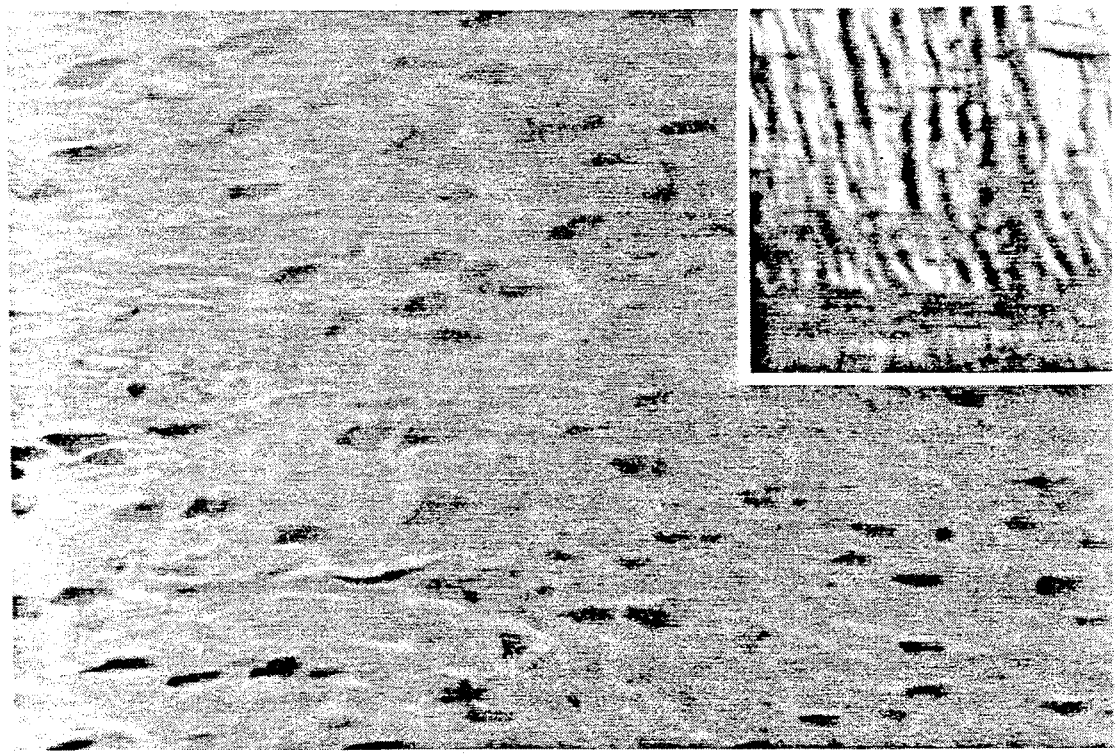
FIG. 3 shows DHT3-Cl implant appearance at 20 weeks post implantation (magnification 40×). Note that no implant is visible. The implant has been replaced by new collagenous tissue which is oriented along the longitudinal axis of the neotendon. Crimp has reappeared in the neotendon which resembles that of normal tendon. This is demonstrated in the upper right corner by polarized microscopy (magnification 10×).
Figure 4:
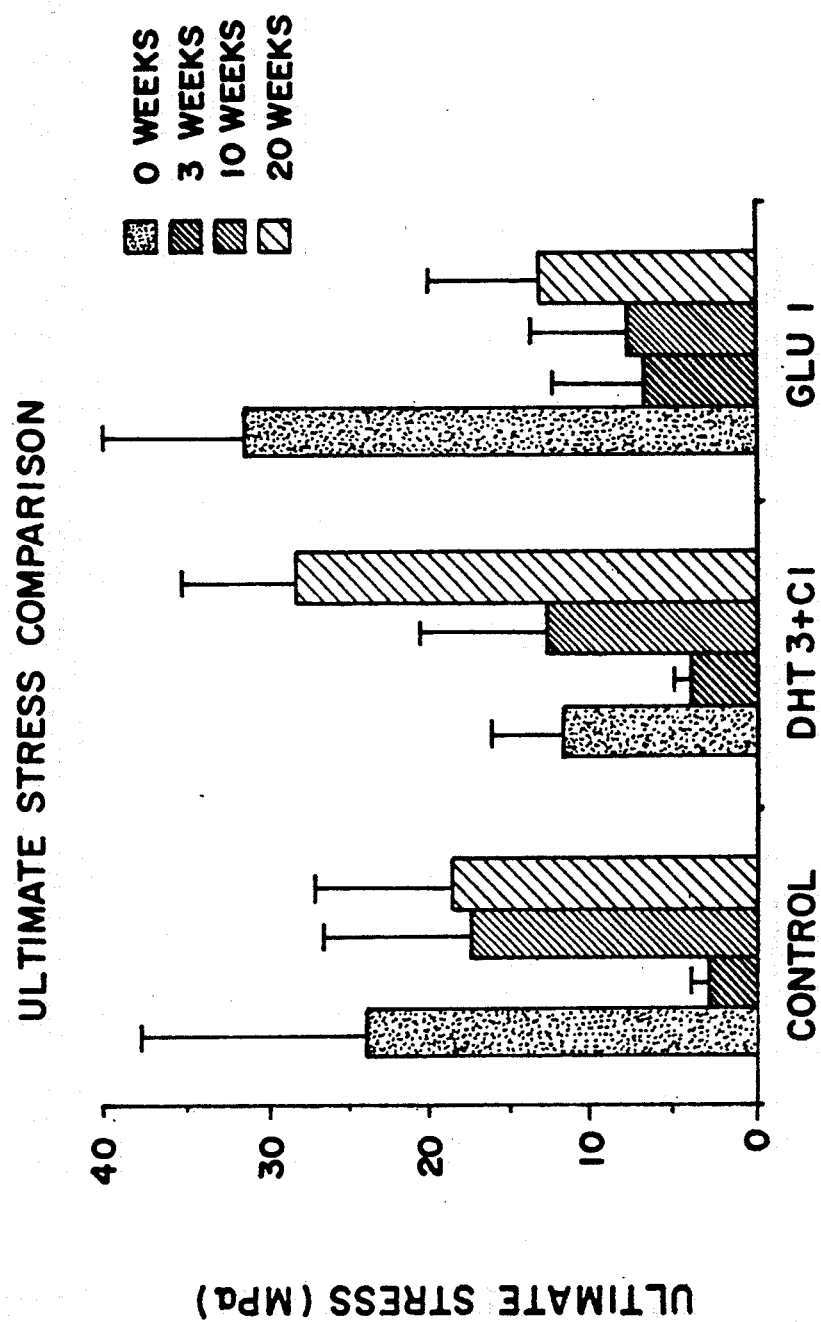
FIG. 4 shows STRESS: This histogram shows means data for each material over the time course between initial implantation and 3,10 and 20 weeks. This is not normalized to the autograft side. Data represents force/cross-sectional area of the implant or autograft at the point of failure.
Figure 5:
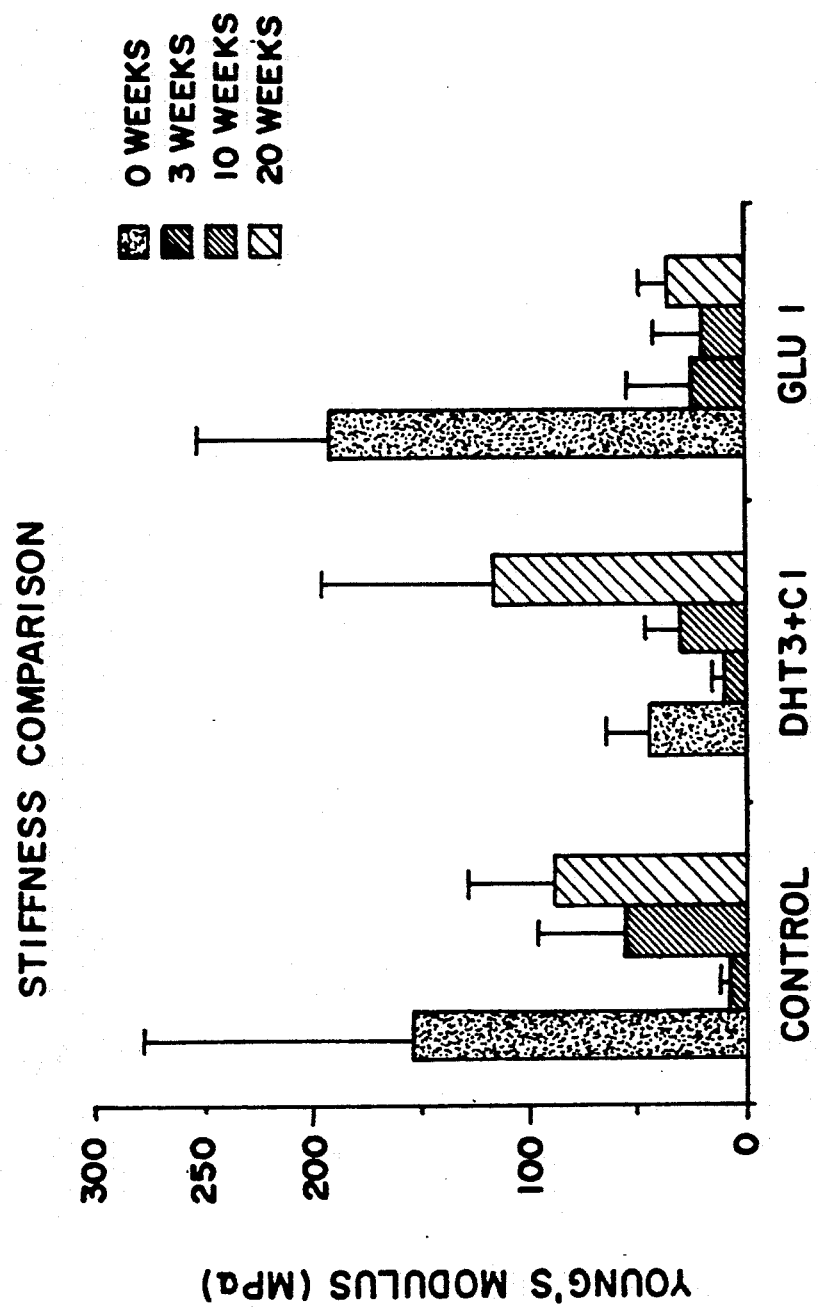
FIG. 5 shows MODULUS: This histogram represents the mean elastic modulus (Force/Displacement) for each material at every time interval. This is not normalized data.
Figure 6:
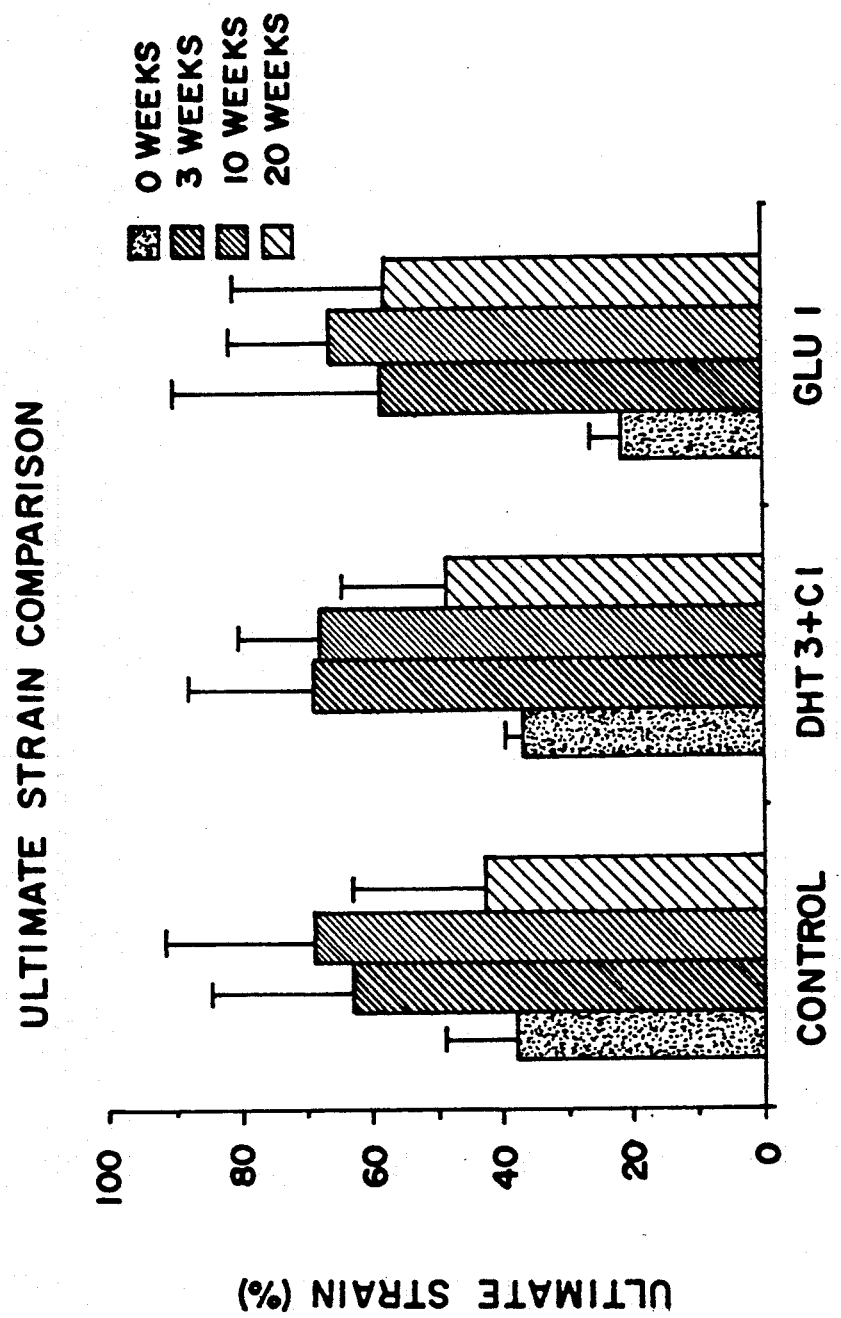
FIG. 6 shows STRAIN: This histogram represents the mean strain (change in length/original length) of each material at every time interval. This is not normalized data.

By three weeks DHT3-Cl implants were invaded by abundant fibroblasts and capillaries. Individual fibers were infiltrated peripherally with fibroblasts and few inflammatory cells. By 10 weeks the implant material could not be found in the neovascular tissue, and fibroblast cellularity was maximal. The DHT3-Cl implant matured and reoriented showing parallel fiber bundles with the appearance of crimp. This was demonstrated by polarized light microscopy. By 20 weeks the neotendon has matured and cellularity decreased to that of normal tendon. The crimp pattern continued to improve (FIG. 3).

Analysis of Mechanical Data

The mechanical properties of each implant were determined on an Instron (model 1122) prior to implementation. Normal tendon values were determined for each animal by testing explants of fresh tendon harvested from the site where synthetic tendons were then implanted. The values of ultimate tensile strength (UTS), modulus of elasticity (MOD), and ultimate strain (STRAIN) were recorded for each explant removed by either 3, 10 or 20 weeks. Means are presented as percent of initial material value upon implantation. FIG. 2 (A,B,C) show non-normalized mechanical.

|  | 3 weeks | 10 weeks | 20 weeks |
|---|---|---|---|
| Autograft |  |  |  |
| UTS | 12.12+/−4.82 | 48.73+/−6.15 | 60.0+/−14.1 |
| MOD | 5.01+/−2.60 | 26.45+/−16.7 | 68.24+/−24.2 |
| STRAIN | 190.5+/−73.2 | 168.0+/−59.2 | 106.3+/−51.8 |
| Glu-1 |  |  |  |
| UTS | 33.64+/−19.6 | 31.68+/−24.4 | 54.34+/−28.7 |
| MOD | 22.68+/−19.9 | 13.83+/−14.6 | 24.23+/−8.68 |
| STRAIN | 190.9+/−65.7 | 175.5+/−38.3 | 151.9+/−60.9 |
| DHT3-Cl |  |  |  |
| UTS | 15.98+/−4.10 | 50.82+/−19.3 | 129.4+/−22.9 |
| MOD | 7.04+/−2.87 | 20.00+/−8.21 | 69.42+/−30.9 |
| STRAIN | 182+/−47.9 | 193.4+/−27.0 | 126.7+/−32.6 |

Autograft Implants

Autograft ultimate tensile strength increased significantly at the 3 to 10 ($p<0.05$) and 3 to 20 ($p<0.05$) week intervals. Modulus improved at all time intervals: 3–10 weeks ($p<0.022$), 10–20 weeks ($p<0.013$), and 3–20 weeks ($p<0.05$). Strain decreased over time but changes were not significant.

Glut-1 Implants

Glut-1 showed no statistically significant increase in tensile strength, modulus or decreas in strain over time.

DHT3-Cl Implants

Increases in tensile strength were significant over each time interval: 3–10 weeks ($p<0.004$), 10–20 weeks ($p<0.05$) and 3–20 weeks ($p<0.05$). Increases in modulus were significant at the 3–10 week ($p<0.010$), 10–20 week ($p<0.009$), and 3–20 week intervals ($p<0.002$). Strain decreased significantly only at the 10–20 week interval($P<0.008$).

Comparison of Materials Over Time

No significant difference between materials was present before 20 weeks. At this time the tensile strength of Glu-1 implants as 54% of its initial strength. At the same time, autograft had 60% of its initial strength and DHT3-Cl was significantly stronger with 129% of its initial strength ($p<0.002$). Similarly DHT3-Cl was significantly stronger than Glu-1 at 20 weeks ($p<0.025$).

At 20 weeks the modulus of autograft was significantly higher than Glu-1 ($p<0.035$). No other significant differences were noted between material modulus or strain at any time interval.

Discussion

Tendon autografts are used to replace the function of a torn ligament or tendon. These are successful even though the graft initially weakens and takes many months to regain tensile strength.

The ideal tendon or ligament implant combines the high strength of synthetic polymer fibers with the scaffold for cellular invasion provided by autogenous grafts. In addition, the regeneration of neotendon is accelerated over that of autograft. This shortens the period of implant protection.

A reconstituted type 1 collagen composite tendon has been designed and implanted. This prosthesis consisted of high strength crosslinked collagen fibers, embedded in a loose uncrosslinked collagen matrix. this implant stimulated new tissue ingrowth in the rabbit achilles tendon model. Under the conditions studied, Glu-1 had slower tissue ingrowth and slower improvement in strength and elastic modulus than autograft. At 20 weeks the implants were still resent within unorganized connective tissue.

DHT3-Cl implants were rapidly invaded and by 20 weeks were totally replaced by crimped collagen neotendon. No evidence of the implant was present. DHT3-Cl strength and elastic modulus increased more quickly than autograft and approached normal tendon values by 20 weeks.

The revascularized autograft under polarized light microscopy exhibited maintenance of crimp. DHT3-Cl implants also showed the development of crimp beginning at 10 weeks and maturing by 20 weeks.

The results indicate that although glutaraldehyde crosslinked implants had higher initial strengths than non-aldehyde crosslinked implants, DHT3-Cl implants had higher strength by 10 weeks and continued to improve.

The animal studies indicate that a crosslinked type I collagen composite synthetic tendon supports the rapid ingrowth of new connective tissue. The neotendon which matures from this implant, simulates the morphological and biomechanical characteristics of normal tendon.

EXAMPLE II

Materials and Methods

Reconstituted Collagen Fibres

Insoluble collagen Type I from fresh, uncured corium was obtained from Devro Inc. (Somerville, NJ, USA). The corium was limed, fragmented, swollen in acid, precipitated, washed with distilled water and isopropanol, lyophilized and stored at $-30°$ C. (33, 34). Collagen-derived peptides were characterized by SDS-PAGE and amino acid analysis as typical of Type I collagen without non-collagenous protein contamination (35).

A 1%(w/v) dispersion of Type I collagen in dilute HCl pH2.0 was prepared by adding 1.2 g of lyophilized collagen to 120 ml of HCl solution in a blender (Osterizer) and mixing at a speed of 10,000 rev min$^{-1}$ for 4 min. The mixture was allowed to settle for 10 min and then remixed at 10,000 rev min$^{-1}$ for 4 min. The resulting dispersion was placed under a vacuum of 0.01 m torr at room temperature to remove any trapped air bubbles. Dispersion is then stored in disposable 30 cc syringes at 4° C.

Collagen fibres were produced by extruding the collagen dispersion through polyethylene tubing with an inner diameter of 0.28 mm into a 37° C. bath of aqueous fibre formation buffer composed of 135 mm NaCl, 30 mm TES (N-tris)(hydroxylmethyl) methyl-2-aminoethane sulphonic acid) and 30 mm sodium phosphate dibasic. The final bath pH was adjusted to 7.5 by adding 5.0 n NaOH drop-wise. Fibres were allowed to remain in the buffer for 45 min, and then placed in 500 ml of isopropyl alcohol for at least 4 h. The fibres were immersed in distilled water for 15–20 min and air dried under tension.

Collagen fibres were cross-linked using glutaraldehyde or by a combination of severe dehydration and treatment with cyanaide. Glutaraldehyde cross-linking was accomplished by placing air-dried collagen fibers in a sealed dessicator containing 10 ml of a 25%(w/v) aqueous glutaraldehyde solution in a pertri dish. The fibres were placed on a shelf in the dessicator and were cross-linked in a glutaraldehyde vapour for 1–4 d at room temperature. Collagen fibres were also cross-linked by placing in an oven at 110° C. and at vacuum of 50–100 m torr for 3 d. Subsequent to dehydrothermal cross-linking (DHT), collagen fibres were placed on a shelf in a sealed dessicator containing a pertri dish with 20 g of cyanamide in 5 ml of distilled water. Collagen fibres were cross-linked for one day in contact with cyanamide vapour (Cl).

Collagen fibres 3–4 cm in length were isolated from the tails of Sprague Dawley rats weighing 200–300 g by dissection under a microscope. The skin was stripped from the tail and tendons were removed using a wire stripper placed on free end of the tail (end opposite dissected stump). Tendons were greatly clamped using the wire strippers placed on the free end of the tail and pulled free from the rest of the tail. Each tendon bundles was split in half along its axis repeatedly until the fiber diameter was about 50 um. Rat tail tendon (RTT) fibres were air dried overnight by hanging the free ends over glass coverslips.

Mechanical testing

Strtess-strain curves for reconstituted collagen fibres and RTT fibres were determined in tension using an Instron Tester Model 1122. Fibers were tested dry and in phosphate-buffered saline (PBS) pH 7.5 using a gauge length of 2 cm and strain rates of 10, 50 and 100% per min. Load extension curves obtained from the chart recorder as well as original cross-sectional areas determined by light microscopy were used to calculate stress-strain behavior, ultimate tensile strength (UTS) and tensile modulus. For area calculations it was assumed that the fibres were circular. It was also assumed that the modulus was equivalent to the tangent to the stress-strain curve in the linear region.

Air-dried fibers were mounted on paper 'frame' by gluing the ends of the fibres to a vetical line drawn on the frame using an epoxy adhesive. The gauge length was determined by the vetical dimension of the window in the frame. Fiber diameters were determined dry and in PBS at three different locations within the window by comparison with the grid lines in a calibrated eyepiece of a microscope. Diameters of wet fibres were measured after immersion in PBS for at least 15 min.

Frames containing specimen fibers were then placed between the upper and lower pneumatic grips of the Instron at a pressure of 40 psi. The sides of the frame were then cut leaving the fibres intact. Fibers were sprayed with PBS before testing. Between 8 and 13 fibres were tested for each strain rate and treatment studied.

Moduli were determined by taking a best-fit tangent to the load-extension curve. A two-tailed Students t-test (p=0.01) was used for statistical evaluation of mechanical data.

Results

Typical stress-strain curves are shown (FIG. 7) for reconstituted collagen fibres cross-linked dehydrothermally for 3 d and with cyanamide for 1 d (DHT3+Cl), fibres cross-linked with glutaraldehyde for 2 and 4 d (Glut 2 and Glut 4) as well as for RTT fibres. An almost linear relationship between stress and strain is observed for wet and dry RTT and wet reconstituted collagen fibres, while the stress-strain behaviour of dry reconstituted collagen fibres is highly non-linear.

FIGS. 8–11 summarize the mechanical properties in tension of wet and dry RTT fibres and reconstituted collagen fibres. The ultimate mechanical properties were found to be independent of strain rate for strain rates between 10% and 100% per min.

The ultimate tensile strength (UTS) of wet glutaraldehyde cross-linked reconstituted fibers ranged from 50 to 66 MPa. Fibres cross-linked by a combination of dehydrothermal and cyanamide treatment (DHT3+Cl) had wet tensile strengths of 24–31 MPa. UTS values for RTT fibers ranged from 33 to 39 MPa. Ultimate strains for reconstituted collagen fibres ranged from 14 to 18% while those for RTT were only 7 to 8%. Moduli for reconstituted collagen fibres ranged from 170–200 MPa (DHT3+Cl) to 384–503 MPa (Glut 2 and Glut 4) and were below those observed for RTT (478–570 MPa). However, moduli values for RTT were not significantly different from those observed for glutaradehyde cross-linked collagen fibers.

Observation

It is known that collagen fibres form structural networks throughout the body that limit tissue deformation and prevent mechanical failure. The structural stability of collagen fibres is a consequence of the triple-helical structure of the molecule, high content of imino acid residues, organized packing of individual molecules into fibrils and the presence of cross-links within collagen fibrils that prevent intermolecular slippage. Results of in vitro studies on collagen self-assembly indicates that fibrils formed by heating collagen solutions, to 37° C. at neutral pH under optimum conditions result in reconstituted collagen fibrils with a structure identidal to that of collagen fibrisl observed in tendons.

In the work involving this invention, the mechanical properties of collagen fibers were evaluated. The fibers were prepared under conditions that have been shown to be optimum for formation of collagen fibres that are characterized by the positive staining pattern of collagen in tissues. The strength of reconstituted collagen fibers was compared with that of fibers derived from tendon.

Rat tail tendon (RTT) fibres are used in this study, since it is possible to dissect fibres as small as 50 um in diameter from RTT without tearing the structure apart.

The results show that reconstituted collagen fibres of small diameter of the invention have ultimate tensile strengths that are approximately equal to those of RTT fibres (30–40 MPa). This is achieved in accordance with the process of the invention by extensive cross-linking with either glutaraldehyde or severe dehydration in combination with cyanamide treatment. The higher tensile strength of RTT in the dry state and the lower elongation at failure compared with that observed for reconstituted collagen fibers suggests that the degree of crystallinity is higer for RTT fibers than for the reconstituted fibres. Crystallinity may in part be introduced during drying before the sample is mounted for mechanical testing.

Reconstituted collagen fibres of high strength and small diameter are needed in the design of biomaterials that enhance the deposition of repair tissue in skin, tendon and the cardiovascular system. Although high-strength oriented and unoriented collagenous materials are reported in the literature (43), no report exists of collagen fibres of small diameter that can be processed into woven and non-woven textile prostheses.

The effects of two different cross-linking procedures on mechanical properties of reconstituted collagen fibres were compared. Glutaraldehyde reacts with free amino-containing groups on collagen and polymerizes to produce cross-links that can span the distance between two molecules (44). The major drawback to glutaraldehyde cross-linking is the moderate inflammatory response that is generated by the residual glutaraldehyde that is released into tissues upon implantation.

An alternative cross-linking process was used which involves severe dehydration in combination with cyanamide treatment. In theory, cyanamide acts as a catalyst in the formation of peptide bonds and is converted into urea after the reaction is completed. Collagen cross-linked using this method evokes an acceptable infammatory response when tested subcutaneously or on excised wounds.

This work indicates that reconstituted collagen fibres can be made which have a small diameter, wet tensile strengths of up to 66 MPa and maintain elongation at failure of about 15%. These fibres are useful as disclosed herein the repair of dermal, dental, cardiovascular, muscular and othopaedic structures.

EXAMPLE III

Materials and Methods

Extraction of Soluble type I Collagen

Acid soluble type I collagen was extracted from tail tendons of young rats as described previously (73). Briefly, the tendons were stripped from the tails and dissolved in 0.01M HCl at 4° C. followed by centrifugation for 30 min. at 30,000×g. The supernatant was sequentially filtered through 0.8, 0.65, and 0.45 um Millipore filters. The collagen preparation was analyzed by SDS polyacrylamide gel electrophoresis and amino acid analysis (73).

Purification of Insoluble type I Collagen

The raw material (bovine corium) was prepared from fresh uncured bovine hide which was obtained from Devro, Inc., Somerville, NJ. The hides were split into two components, the grain layer (papillary dermis) and the corium (reticular dermis). Fresh corium was frozen and stored at −20° C. until it was used.

One liter of the frozen raw material was defrosted at room temperature and place in an 18 liter Nalgene processing tank (Consolidated Plastics, Twinsburg, OH), equipped with air and water lines. Distilled water was added until the total volume of the processing mixture reached 14 liters. Air at a pressure of 6 psi was introduced into the tank for 5 minutes, to create a homogeneous mixture. This mixture was then left to sediment for 20 minutes. After complete sedimentation occurred, the liquid phase was drained and fresh distilled water was added until the total volume reached 14 liters. This procedure was repeated three times.

Eight liters of 99.8% of isopropyl alcohol (Mallinkroft, Inc., Paris, KY) was added to the solid phase; the sediment was mixed using air in a tank placed on a gyrotory shaker (New Brunswick Scientific Co., New Brunswick, NJ) for 12 hours at a speed of 34 rev./min.

The liquid phase was then removed using a Becton siphon pump (Consolidated Plastic, Twinsburg, OH) and 8 liters of 99.8% isopropyl alcohol was mixed with the solid phase. The mixture was then placed on the shaker for another 12 hours.

After removal of the liquid phase, the material was washed with 2 liters of distilled water, poured into plastic trays and placed in a freezer until frozen solid.

The frozen material was then placed in the cold trap of a freeze dryer (Freeze Mobile 12, Virtis, Inc., Gardner, NY) at −65° C. A vacuum of 10 microns was then applied for 48 to 96 hours. The vacuum was then released and material removed. The freeze dried collagen was removed from the trays and stored in air tight bags.

Preparation of Insoluble type I Collagne for Fiber Formation

A 1N solution of HCl was slowly added to 120.0 ml of distilled water until the pH was 2.0. A 1.2 g sample of insoluble type I collagen, extracted by the procedure described above, was then put into a blender (Osterizer Model, Oster Corporation, Milwaukee, WI) with the HCl (pH 2.0). This 1% w/v collagen HCl dispersion was blended at high speed (10,000 rpm) for 3 minutes.

The dispersion was then emptied from the blender into a 600 ml sidearm flask. A vacuum (Vacuum Pump, Model 150, Precision Scientific Company, Chicago, IL) of 100 microns was applied at room temperature until the air bubbles were removed from the dispersion. This procedure required approximately 15 minutes. The vacuum was removed and the dispersion was ready for making fibers.

Glycosaminoglycans and Proteoglycans

Dermatan sulfate (chondroitin sulfate B from porcine skin), chondroitin sulfate (type A from whale cartilage), glycosaminoglycans (GAG) and dextran sulfate (Dexs) were obtained from Sigma Chemical Company, St. Louis, MO. Chondroitin sulfate proteoglycan (CS-PG) and dermatan sulfate proteoglycan (DS-PG) from hypertrophic scar tissue and high molecular weight proteoglycan from articular cartilage (PGl) were prepared and characterized as previously described (76,77). Dermatan sulfate proteoglycans from scar had molecular weights of 30,000. Chondroitin sulfate proteglycan from scar contains about 10% of hexuronic acid residue as iduronic acid and has a molecular weight of 78,000 based on chromatography on Sepharose CL-6B. High molecular weight proteoglycan from articular cartilage had a molecular weight of 1,200,000. Dextran sulfate was used in these studies as a high molecular weight analog of sulfated glycosaminoglycans.

Fibril Assembly Studies

Turbidity-time studies

Lyophilized soluble type I collagen was dissolved at 1 mg/ml in HCl, pH 2.0, stirred t 4° C. for 24 hours, dialyzed against HCl, pH 2.0, centrifuged at 1600 g for 60 minutes and the supernatant was then filtered through a 0.65 um Millipore filter. This collagen stock solution was stored at 4° C. for periods of up to one week.

Fibril formation was initiated by mixing 0.9 ml of a collagen solution with 0.1 ml of buffer on ice to give a final composition of 30 mM n-tris[hydroxymethyl]-methyl-2-aminoethanesulfonic acid (TES), 30 mM phosphate and NaCl to a final ionic strength of 0.225 at pH 7.3. Cuvettes were filled with sample, sealed and transferred to a water-jacketed sample compartment of a Gilford Model 250 spectrophotometer. The compartment was maintained at the desired experimental temperature and the absorbent was recorded as function of time. Absorbent was defined as the natural logarithm of the ratio of the incident light and the scattered light intensities. Absorbent at 313 nm was converted to turbidity by multiplying by 2.303.

Collagen concentrations between 0.20 and 0.45 mg/ml and proteoglycan concentrations between 0.001 and 0.2 g/100 m were evaluated at temperatures from 27° to 37° C.

Extrusion of collagen fibers

An aqueous fiber formation buffer composed of 135 mM NaCl, 30 mM TES and 30 mM sodium phosphate dibasic at a final pH of 7.5 was heated to 37° C. in a temperature controlled water bath. Glycosaminoglycan (concentrations between 0.001 and 0.2 g/100 ml) or proteoglycan (concentrations between 0.01 and 0.02 g/100 ml) was added to the fiber formation buffer and stirred. A 1% w/v collagen dispersion (1 g/100 ml) was placed in a syringe to which a polyethylene tubing (Clay Adams, PE-50) of internal diameter 0.58 mm was attached. A syringe pump (Sage Instruments, model 341A) at a speed of 7 ml/minute was used to extrude the fibers into fiber formation buffer. Extruded fibers were left in the tray containing fiber formation buffer maintained at 37° C. for 60 minutes. Fiber formation buffer was then emptied out from the tray using a vacuum hose and was replaced by isopropanol and left overnight. Isopropanol was removed and was replaced by distilled water for 15 minutes. Fibers were then removed from distilled water and air dried under tension.

Collagen Fiber Crosslinking

Extruded collagen fibers were crosslinked by exposure to glutaraldehyde vapor for 24 hours (Glut 1) at room temperature in a sealed dessicator as described previously (78).

Measurement of fiber diameter

Mean collagen fiber profile widths (an estimate of diameter) were measured dry and in phosphate buffered saline solution (PBS) at three different locations within the window by comparison with the grid lines in a calibrated eyepiece of a microscope (Leitz, Laborlux 12 Pol). Diameters of wet fibers were measured after immersion in PBS for 15 minutes.

Mechanical Testing of Fibers

Stress-strain curves for reconstituted collagen fibers were determined in tension using an Instron Tester Model 1122 (Instron Corporation, Canton, MA.) Fibers were tested dry and in phosphate buffered saline solution at pH 7.5 (PBS) usin a gage length of 2 cm and strain rate of 10% per minute. Load-extension curves obtained from the chart recorder as well as original cross-sectional areas determined by light microscopy were used to calculate stress-strain behavior, ultimate tensile strength (UTS), and tensile modulus. For area calculations it was assumed that the fibers were circular in cross-section. It was also assumed that the modulus was equivalent to the tangent to the stress-strain curve in the linear region.

Air dried fibers were mounted on a paper "frame" by gluing the ends of the fibers to a vertical line drawn on the frame using an epoxy adhesive as described previously (78). The gage length was determined by the vertical dimension of the window in the frame.

Frames containing specimen fibers were then placed between the upper and lower pneumatic grips of the Instron at a pressure of 40 psi. The sides of the frame were then cut leaving the fibers intact. Fibers were sprayed with PBS prior to testing for each treatment studied. Moduli were determined by taking a best fit tangent to the load-extension curve in the linear region.

Birefringence Retardation Measurements

Fibers were examined under polarized light in the presence of a Leitz X/10 Brace-Kohler calibrated compensator. The image was observed on a video display screen connected to a Venus TV-2M camera fitted to a Leitz 12 Pol microscope with a X32 objective lens. After zeroing the compensator, the fiber to be measured was rotated to a position of maximum extinction, and then oriented diagonally by turning the stage 45° counterclockwise. The determined angle of rotation ($w_o$) was measured by turning the Brace-Kohler compensator drum until maximum extinction of the specimen was observed. The phase difference (T), was approximated using the following formula:

$T = T_o \sin 2w_o$, where $T_o$ is the polychromatic light calibration value of 71.84 mm for the Brace-Kohler compensator.

The volume fraction of collagen in a fiber was calculated using the following formula derived for a series of parallel rods (79) assuming that the intrinsic birefringence was negligible compared to the form birefringence.

$$T/T = [n_2^2 + V_f(n_1^2 - n_2^2)]^{\frac{1}{2}} - [n_2^2 + (A/B)]^{\frac{1}{2}}$$

where $A = V_f(n_1^2 - n_2^2)$ and
$B = 1 + ((1 - V_f)(n_1^2 - n_2^2)(0.5)/n_2^2)$ $V_f$ is the volume fraction of the rods, $n_1$ is the refractive index of the rods ($n_1 = 1.618$ for collagen), $n_2$ is the refractive index of air ($n_2 = 1.00$), T is the thickness of the fiber, and T is birefringence retardation.

Uronic Acid Assay

Uronic acid was used to determine the proteoglycan content of collagen fibers extruded in vitro. Uronic acid was measured using the carbazole method (33) which has been determined to be sensitive to a concentration of 0.004 umoles/ml.

A 1.0 ml sample containing 0.02-0.2 micromole of uronic acid was treated with 5 ml of the 0.025M sodium tetraborate, prepared in concentrated sulfuric acid. After thorough mixing, the solution was heated for 10 minutes in a boiling water bath, cooled to room temperature, and 0.2 ml of the 0.125% carbazole solution prepared in ethanol was added. The resulting solution was heated for 15 minutes in a boiling water bath, cooled to room temperature, and the optical density read at 530 nm. A calbration curve of optical density versus concentration was determined for each proteoglycan.

Studies were conducted to determine the effects of GAGs and PGs on the nucleation of collagen fibrils and growth of fibrils into fibers.

Turbidity-time studies were used to study the effect of PGs on fibril nucleation while mechanical properties and birefringence retardation determinations were used to study the effects of GAGs and PGs on the properties of collagen fibers.

Turbidity-time studies

Figure 12:
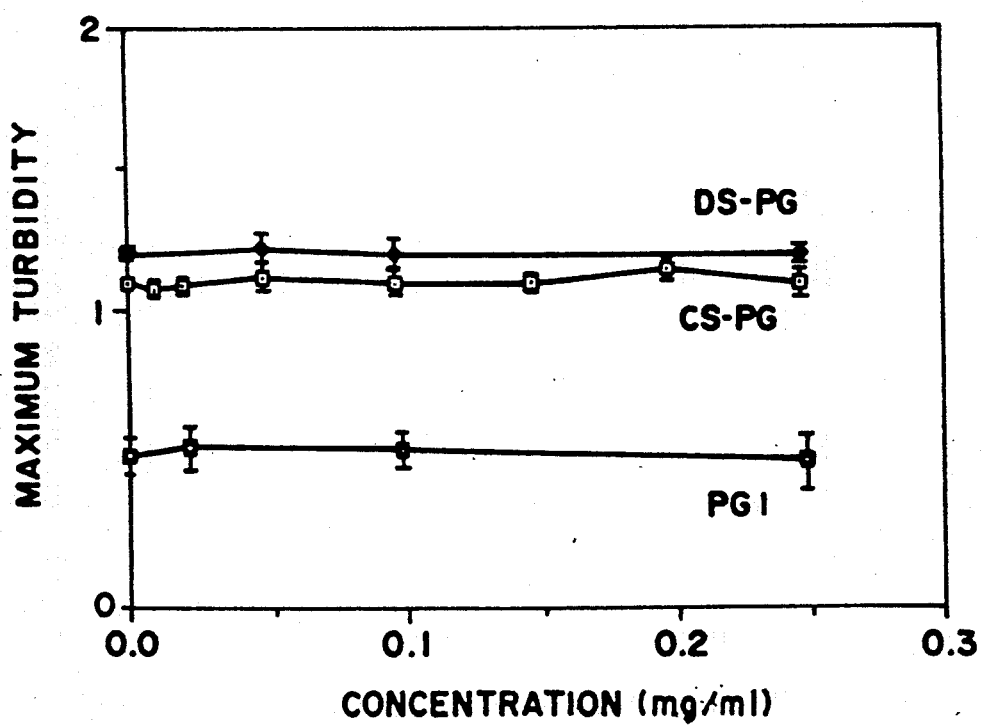
FIG. 12 shows Maximum turbidity versus proteoglycan concentration. Plot of maximum turbidity at 313 nm versus proteoglycan concentration in mg/ml for high molecular weight proteoglycan from articular cartilage (PGl-PG) and dermatan sulfate (DS-PG) and chondroitin sulfate (CS-PG) proteoglycans from scar. Error bars show typical standard deviations.

In these studies PGs were added to neutral solutions containing soluble collagen under conditions that promote nucleation and growth of fibrils. PG1, a high molecular weight proteoglycan from articulr cartilage, CS-PG and DS-PG from hypertrophic scar tissue over concentration ranges of 0.001 to 0.25 mg/ml were used to study collagen fibrillogenesis. Over this range of concentration to maximum turbidity, a measure of fibril diameter was not affected by PGs (CS-PG, DS-PG and PG1) (see FIG. 12).

Collagen Fiber Extrusion Studies

In these studies insoluble collagen containing preformed nuclei in an acidic dispersion is extruded into a fiber formation buffer containing GAGs and PGs. Insoluble bovine hide collagen was previously characterized as type I collagen containing no detectable non-collagenous proteins based on sodium dodecyl sulfate gel electrophoresis and amino acid analysis (78). Collagen fibers formed in the presence of GAGs and PGs were characterized by determination of polymer volume fraction ($V_f$), mechanical properties, and uronic acid content as discussed below.

Birefringence Retardation Measurements

Figure 13:
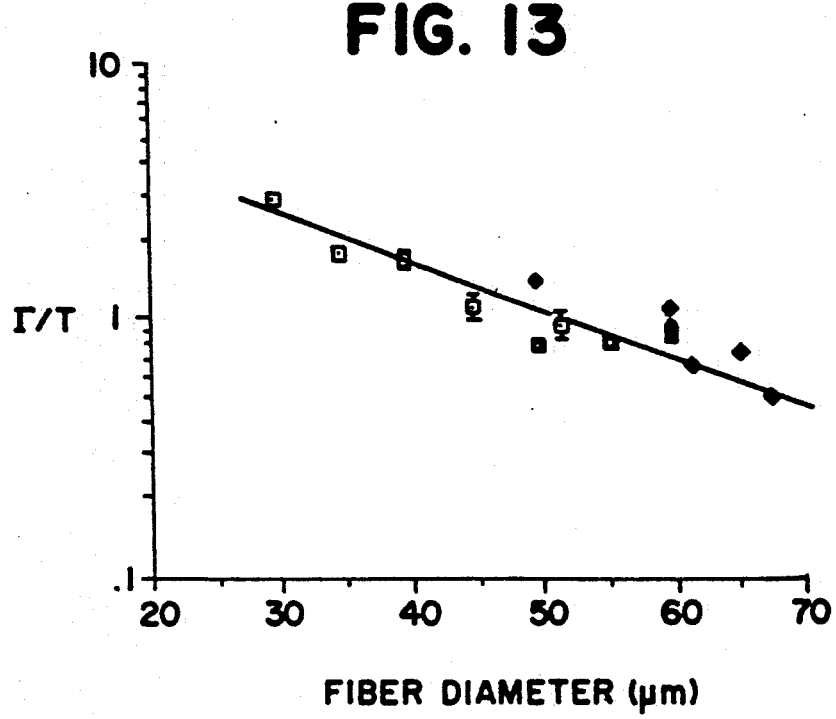
FIG. 13 shows birefringence retardation versus dry fiber diameter. Plot of log birefringence per unit fiber diameter ( /T) versus dry diameter for control collagen figer ( ) and collagen fiber containing dextran sulfate ( ), chondroitin sulfate ( ), and dermatan sulfate ( ). Error bars show typical standard diviations for measurement of birefringence per unit fiber diameter.

Birefringence retardation per unit thickness was found for crosslinked collagen fibers and fibers containing dermatan, chondroitin and dextran sulfate. Birefringence retardation per unit fiber thickness was found to be independent of GAG concentration at a 0.99 confidence level except for dextran sulfate concentrations of 0.01% and 0.001% w/v (see FIGS. 19, 20. 21) based on a student's t-test. In the presence of 0.01% PG1 or chondroitin sulfate PG the birefringence retardation per unit fiber thickness are not statistically different at a 0.01 confidence level (see Table 22). Birefringence retardation of fibers formed in the presence and absence of PGs and GAGs are found to be strongly dependent on fiber diameter (see FIG. 13).

Figure 14:
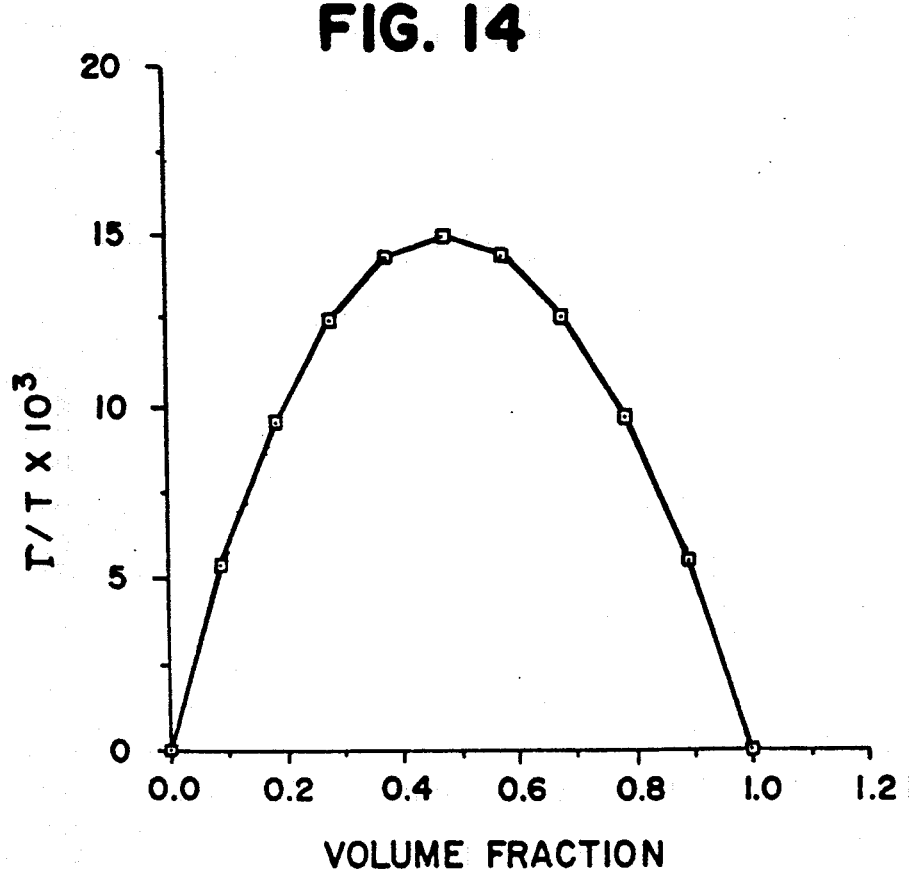
FIG. 14 shows birefringence retardation per unit fiber diameter ( /T) versus volume fraction of collagen. Plot of /T versus volume fraction of collagen obtained using equations derived for a series of parallel rods (32) as discussed in Methods. It was assumed that the volume fraction of collagen in dry fibers was greater than 0.2.

Volume fraction of collagen in fibers was calculated from the birefringence retardation per unit fiber thickness from FIG. 14. It was assumed that the volume fraction ($V_f$) of collagen was greater than 0.2 since the measurements were made in the absence of solvent. As shown in FIG. 23 values of $V_f$ range from 0.95 for control fibers to 0.98. This small variation in $V_f$ is not statistically significant and due primarily to decreased values of birefringence retardation/unit fiber diameter with increased diameters.

Mechanical Testing

Figure 15:
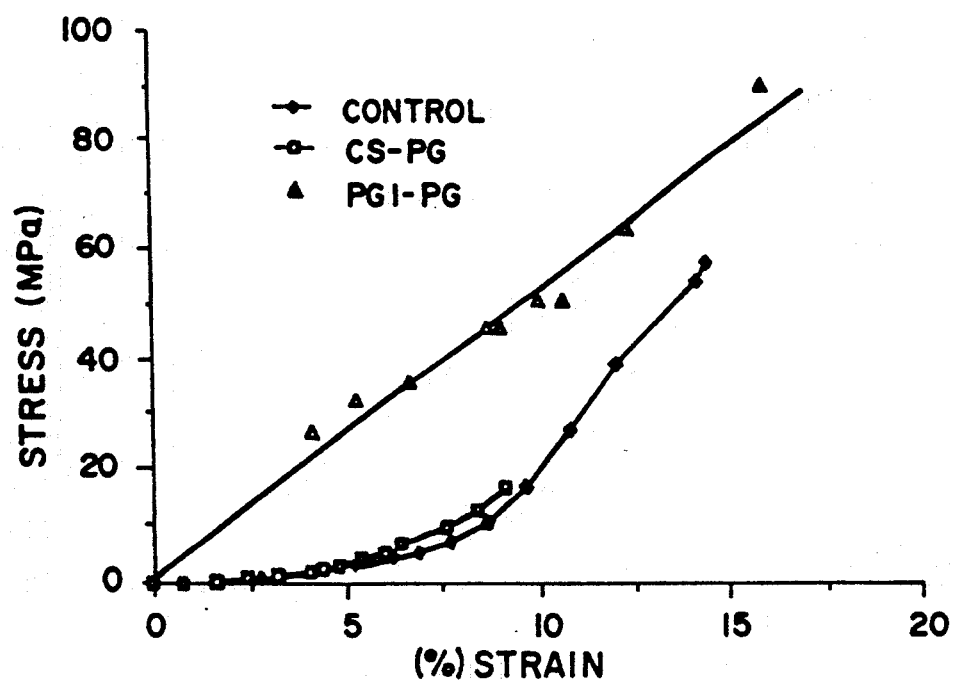
FIG. 15 shows Stress-strain curves of collagen fibers. Typical stress-strain curves of control collagen fibers and fibers extruded into fiber formation buffer containing chondroitin sulfate proteoglycan from scar (CS-PG) or containing high density proteoglycan from articular cartilage (PGl-PG). Measurements were made in uniaxial tension at room temperature and at a strain rate of 10% per minute.
Figure 16:
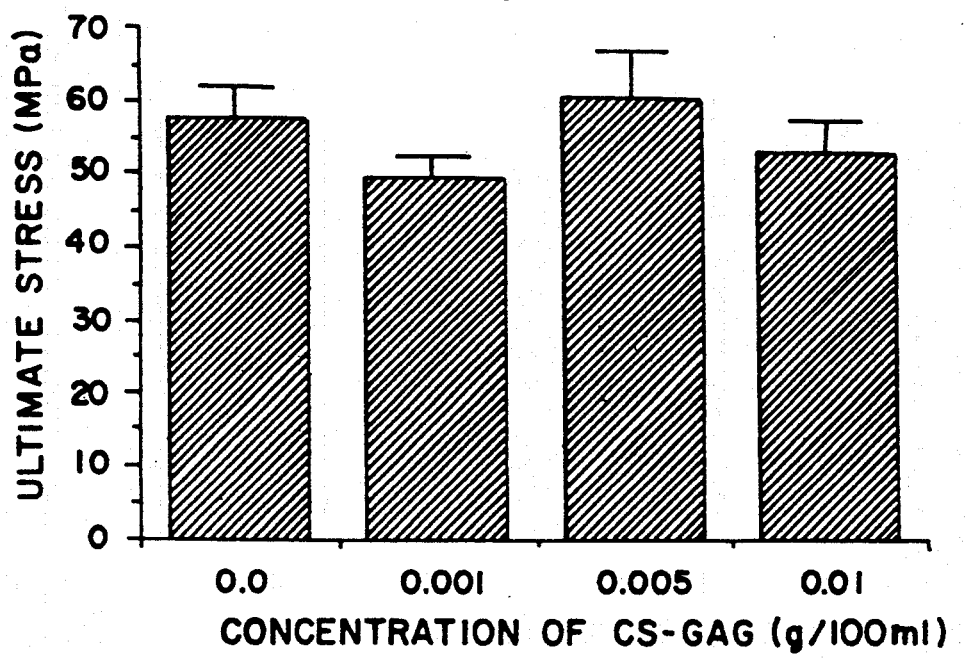
FIG. 16 shows ultimate tensile stress versus glycosaminoglycan concentration. Plot of tensile strength obtained from uniaxial tensile measurements similar to those shown in FIG. 4 as a function of chondroitin sulfate (CS-GAG) concentration (5a), concentration (5b). Error bars represent standard deviations of the mean.
Figure 17:
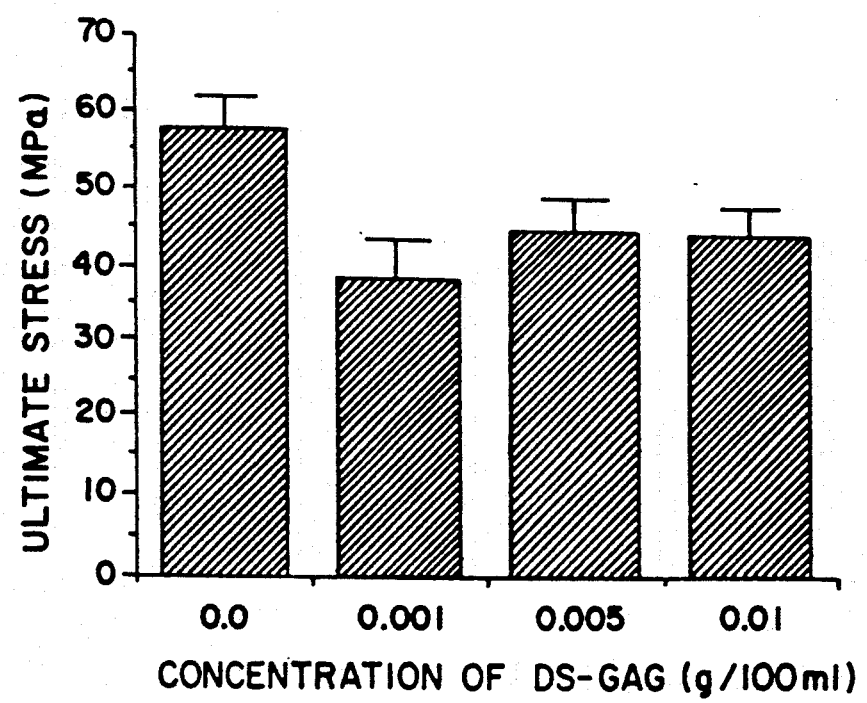
FIG. 17 shows ultimate tensile strength versus glycosaminoglycan concentration. Plot of tensile strength obtained from iniaxial tensile measurements similar to those shown in FIG. 15 as a function of dermatan sulfate (DS-GAG) concentration. Error bars represent standard deviations of the mean.

Typical stress-strain curves for crosslinked collagen fibers in the presence and absence of GAGs and PG1 are shown in FIG. 15. In the presence of chondroitin sulfate the ultimate tensile strength (UTS) of the fibers was similar to that of control fibers (see FIG. 16). UTS of fibers containing dermatan sulfate were lower than the values for the control at a 0.95 confidence level. UTS of fibers extruded in the presence of dextran sulfate was observed to be approximately 50% of control collagen fibers (results not shown). UTS of crosslinked (Glut1) fibers without CS-PG (control) was observed to be approximately 6 fold higher than crosslinked (Glut1) fibers extruded in the presence of CS-PG.

Figure 18:
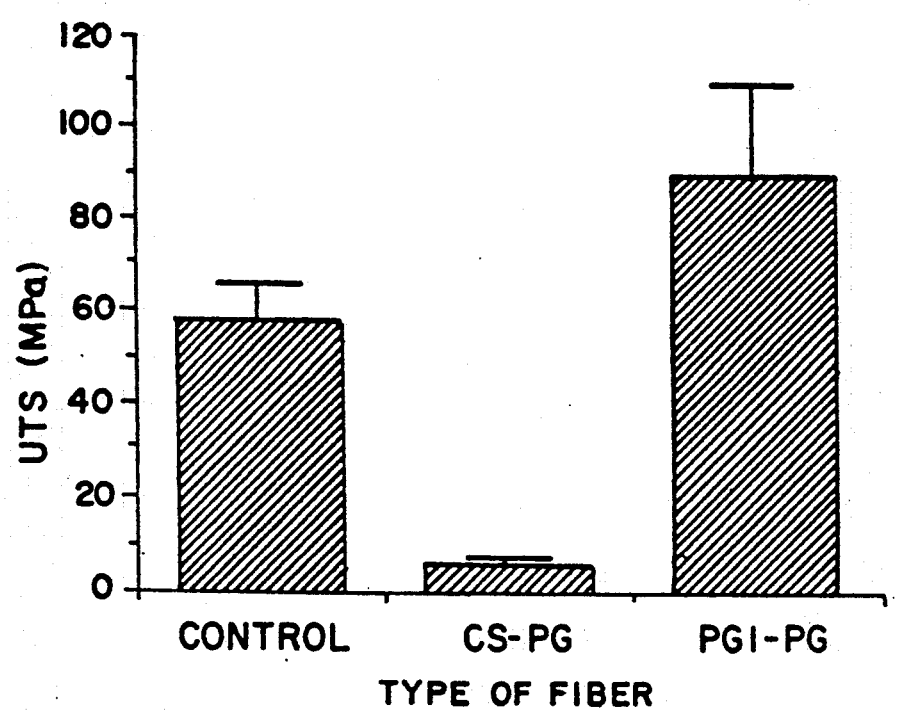
FIG. 18 shows ultimate tensile strength versus proteoglycan type. Plot of tensile strength obtrained from uniaxial tensile measurements similar to those shown in FIG. 4 for collagen fiber (control) and fiber containing chondroitin sulfate proteoglycan from scar (CS-PG) and high density proteoglycan from articular cartilage (PGl-PG). Error bars represent standard deviations of the mean.

In comparison, it was found that crosslinked fibers which were extruded in presence of PG1 showed a 1.5 fold increase in the UTS compared with controls (see FIG. 18). FIG. 24 summarizes mechanical strength data for fibers containing CS-(PG) and PG1. Modulus values calculated in the linear region of stress-strain curves for fibers extruded in presence of CS-PG were lower as compared to fibers without PGs. Modulus values calculated for fibers with PG1 were higher as compared with controls. Percentage strain at break for crosslinked fibers extruded in presence of CS-(PG) was slightly lower than controls whereas fibers prepared with PGl did not show any significant difference in percentage strain compared with the controls.

It is observed that the fibers of the invention which were treated with PGl had a remarkably high UTS (MPA) value (90.4±21.4).

Uronic Acid Content Detemination

The amount of GAG of PG associated with extruded collagen fibers was determined from a standard calibration curve constructed from uronic acid analysis conducted for each macromolecule. As indicated in Table 25 the amount of PGs attached to collagen fibers ranged from about 0.3 to about 0.8 (% w/w) and was significantly different thant the control at the 0.99 confidence level. GAG concentrations present on collagen fibers were also less than 1% (data not shown). This is another distinctive characteristic of the fibers which are particularly useful in the invention.

The work carried out in conjunction with this invention shows that high molecular weight chondroitin sulfate proteoglycan (PGl) from articular cartilage influences the later stages of collagen fiber formation and leads to a fiber with increased tensile strength compared to controls or collagen fibers formed in the presence of low molecular weight chondroitin sulfate proteoglycan from scar. Mechanical studies suggest that the presence of high molecular weight chondroitin sulfate proteoglycan appears to lead to efficient stress transfer between collagen fibrils. This work confirms that collagen fibers formed in the presence of low amounts of high molecular weight chondroitin sulfate proteoglycan are useful in tendon or ligament prothesis where high tensile strength is an important design criteria.

The publications listed on the following pages are of interest in conjunction with the invention.

REFERENCES

1. Arnoczy, S. P.; Rubin, R. M.; and Marshall, J. L.: Micorvasculature of the Cruciate Ligaments and its response to injury. An Experimental Study in Dogs.: *JBJS* 61-A,8:122–1228, 1979.
2. Arnoczy, S. P.; Warren, R. F.; and Ashlock, M. A.: Replacement of the Anterior Cruciate Ligament Using a Patellar Tendon Allograft.: *JBJS* 68-A,3:376–385,1986. 3.
3. Clancy, W. G. Jr.; Narechania, R. G.; Rosenberg, T. D., et al.: Anterior and Posterior Cruciate Ligament Reconstruction in Rhesus Monkeys.: *JBJS*63-A,8:1270–1284, 1981.
4. Doillon, C. J.; Dunn, M. G.; Bender, E.; and Silver, F. H.: Collagen Fiber Formation in Repair Tissue: Development of Strength and Toughness,: *Collagen Res. Rel.* 5:481–492, 1985.
5. Doillon, C. J.; Dunn, M. G.; Berg, R. A.,; and Silver, F. H.: Collagen Deposition During Wound Repair.: *SEM* 2:897–903, 1985.
6. Doillon, C. J.; and Silver, F. H.: Collagen-Based Wound Dressing; Effects of Hyaluronic Acid and Fibronectin on Wound Healing.: *Biomaterials,* 7, 1:307, 1986.
7. Doillon, C. J.; Whyne, C. F.; Berg, R. A.; Olson, R. M.; and Silver, F. H.: Fibroblast-Collagen Fibers in Vitro and in Vivo.: *SEM* 3:1313–1320, 1984.
8. Feagin, J. A.; and Curl, W. W.: Isolated Tear of the Anterior Cruciate Ligament-5 year Follow-up Study: *Sports Med* 4,3:95–100, 1976.
9. Friedman, M. A.; and Ferkel, R. D.: Prosthetic Ligament Reconstruction of the Knee, Philadlephia, *W. B. Saunders,* 1988.
10. Gelman, R. A., Poppke, D. C., and Piez, K. A.: Collagen Fibril Formation in Vitro, the Role of the Non-Helican Terminal Regions.: *J. Biol. Chem.* 254: 11741–11745, 1979.
11. Goodship, A. E.; Wilcock, S. A.; and Shah, J. S.: The Development of Tissue Around Various Prosthetic Implants Used as Replacements for Ligaments and Tendons: *COOR* 196:61–68, 1985.
12. Hughes, K. E.; Fink, D. J.; Hutson, T. B; and Veis, A.: Oriented Fibrillar Collagen and its application to Biomedical Devices.: *J. Amer. Leather Chemists Asso.:*70:146–158, 1985.
13. Kato, Y. P.; Christiansen, D. L.; Hahn, R. A.; Shieh, S. J.; Goldstein, J. D.; and Silver, F. H.: Mechanical Properties of Collagen Fibers: A Comparison of Reconstituted and Rat Tail Tendon Fibers.: *Biomaterials,* in press, 1988.
14. Kennedy, J. C.; Roth, J. H.; Mendenhall, H. V.: Intraarticular Replacement of the Anterior Cruciate Ligament-Deficient Knee.: *Amer. J. Sports Med.:* 8,1: 1–8, 1979.
15. McMaster, W. C.; A histologic Assessment of Canine Anterior Cruciate Substitution with Bovine Xenograft.: *COOR* 196:196–201, 1985.
16. McMaster, W. C.; Kouzelos, J.; Liddle, S.: Tendon Grafting with Glutaraldehyde Fixed Material.: *J. Biomed. Mater. Res.:*10:259–271, 1976.
17. Mendes, D. G.; Iusim, M.; Angel, D., et al: Histologic Pattern of Biomechanic Propertes of the Carbon Fiber-Augmented Ligament Tendon: *COOR* 196:51–60, 1985.
18. Noyes, F. R.; Mooar, P. A.; Matthews, D. S.; Butler, D. L.: The Symptomatic Anterior Cruciate Deficient Knee: *JBJS* 65A, 2;154–174, 1983.
19. Rodkey, W. G.; Cabaud, E.; Feagin, J. A.; and Perlik, P. C.: A Partially Biodegradable Material Device for Repair and Reconstruction of Injured Tendons.: *Amer. J. Sports Med.* 13,4:242–247, 1985.
20. Van Steensel, C. J.: Failure of Anterior Cruciate Ligament Reconstruction Using Tendon Xenograft.: *JBJS* 69A, 7:860–86, 1987.
21. Weadock, K.; Olson, R. M.; and Silver, F. H.: Evaluation of Collagen Crosslinking Techniques.: *Biomat. Med. Devel. Art. Org.* II,4:293–318, 1983–1984.
22. Silver, F. H.; Biological Materials, Structure, Properties and Modelling of Soft Tissues, NYU press, 1987, Ch. 1, 6, 7.
23. Dunn, M. G; and Silver, F. H., Viscoelastic behaviour of human connective tissue: relative contribution of viscous and elastic components; *Connect Tissue Res.* 1983, 12, 59–70.
24. Jenkins, D. H. R.; Forster, I. W.; McKibbin, B; and Ralis, Z. A., Induction of tendon and ligament formation by carbon Implants, *J. Bone Joint Surg.* 1977, 59.,B, 53–57.
25. Hunter, J. M; and Salisbury, R. E., Flexor-tendon reconstruction in severely damaged hands, *J. Bone Joint Surg.* 1971, 53-A, 829–858.
26. Alexander, H.; Weiss, A. B; and Parson, J. R., Ligament and tendon repair with an absorbable polymar-coated fibrestent, *Bull. Hosp. Joint Dis.* 1986, 46. 155–173.
27. Bolton, C. W; and Bruchman, W. C., The GORETEX expanded polytetrafluoroethylene prosthetic ligament, *Clin. Orthop.* 1986, 196, 203–213.

28. McMaster, W. C.; A histologic xenograft assessment of canine anterior cruciate substitution with bovine, *Clin. Orthop.* 1985, 196, 196-201.

29. Shino, K.; Kimura, T.; Hiorse, H.; Inoue, M.; and Ono, K., Reconstruction of the anterior cruciate ligament by allogenic tendon traft, *J. Bone Joint Surg.* 1986, 68-B 739-746.

30. Amis, A. A.; Campbell, J. R.; Kampson, S. A.; and Miller, J. H., Comparison of the structures of new tendons induced by implantation, *J. Bone Joint Surg.* 1984, 66-B, 131-139.

31. Goodship, A. E; and Cooke, P., Biocompatibility of tendon and ligament prostheses, *CRC Crit. Rev. Biocompat.* 1986, 2, 303-334.

32. Friedman, M. J.; Sherman, O. H.; Fox, J. M.; Del Pizzo; W. Snyder, S. J. and Ferkel, R. J., Autogenic anterior cruciate ligament (ACL) anterior reconstruction of the knee. *Clin. Orthop.* 1985, 196, 9-14.

33. Komanowsky, J. J.; *Am. Leather Chemists Assoc.* 1974, 69, 410-411.

34. Chernomorsky, A., Effect of purification procedure on the biocompatibility of collagen-based biomaterials. MS Thesis, Rutgers University. 1987.

35. Weadock, K.; Olson, R. M.; and Silver, F. H., Evaluation of collagen crosslinking techniques, *Biomater. Med. Devices Artif. Organs* 1984, 11, 293-318.

36. Gross, J., Highberger, J. H. and Schmitt, F. O., Collagen structures considered as states of aggregation of a kinetic unit, *Proc. Natl Acad. USA* 1954, 40, 679-688.

37. Bensusan, H. B.; and Scanu, A.J. *Am. Chem. Soc.* 1960, 82, 4990-4998.

38. Fessler, J. H.; Some properties of neutral salt soluble collagen, *Biochem. J.* 1960. 76, 452-463.

39. Cassel, J. M.; Mandelkern, L.; and Roberts, D. E., The kinetics of the heat precipitation of collagen. *J. Am. Leather Chemists Assoc.* 1962, 57.

40. Wood, G. C., and Keech, M. K., The formation of fibrils from collagen solutions, *Biochem., J.* 1960, 75, 588-598.

41. Gelman, R. A.; Poppke, D. C.; and Piez, K. A., Collagen fibril formation in vigra, the role of the nonhelical terminal regions. *J. Biol. Chem.* 1979, 254, 11741-11745.

42. Silver, F. H.; Type I collagen fibrillogenesis in vitro. *J. Biol. Chem.* 1981, 246, 4973-4977.

43. Hughes K. E.; Fink, D. J.; Hutson, T. B.; and Vels A., Oriented fibrillar collagen and its application to biomedical devices. *J. Am. Leather Chemists Assoc.* 1984, 79, 146-158.

44. Cheung, D. T., and Ninmi, N. E., Mechanism of crosslinking by proteins by glutaraldehyde, *Connect Tissue Res.* 1982, 10, 201-216.

45. Chvapil, M.; Speer, D.; Morva, W and Eskelson, C., Efect of tanning agent on tissue reaction to tissue implanted collagen sponge, *J. Surg. Res.* 1983, 35, 402-409.

46. Doillon, C. J., and Silver, F. H., Collagen-based wound dressing: effects of hyaluronic acid and Oibronection on wound healing. *Biomaterials* 1986, 7, 3-8.

47. Silver, O. H.; Berg, R. A.; Birk, D. A.; Weadock, K., and Whyne, C., Biodegradable-matrix and methods for producing same, U.S. Pat. No. 4,703,108, 1987.

48. Silver, F. H. Biological Materials, Structure, Properties and Modeling of Soft Tissues, NYU Press 1987, Chapters 1, 6 and 7.

49. Vogel, K. G., and Heinegard, G. R. Characterization of proteoglycans from adult bovine tendin, *J. Biol. Chem.*, 1985, 260, 9298-8306.

50. Poole, A. R., Health and disease: structure and fuctions, *Biochem. J.* 1986, 236, 1-14.

51. Harkness, R. D.; Mechanical Properties of Connective Tissues In Relation to Function. In: *Fibrous Proteins*, vol. 1, edited by D. A. D. Parry and L. K. Creamer, Academic Press, NY, p 211-213, 1979.

52. Lapiere, Ch. M.; Nusgens, B., and Pierard, G. E. Interaction between collagen type I and type III in conditioning bundles organization, *Conn. Tissue Res.* 1799, 5, 21-29.

53. Birk, D. E., and Silver, F. H., Collagen fibrillogenesis in vitro: comparison of types I, II and III, *Arch. Biochem. Biophys*, 1984, 235, 178-185.

54. Hayashi, T.; and Nagai, Y. Factors affecting the interactions of collagen molecules as observed by in vitro fibril formation, *J. Biochem.*, 1974, 76, 177-186.

55. Comper, W. D.; and Veis, A. Characterization of nuclei in vitro collagen fibril formation, *Biopolymers*, 1977, 16, 2133.

56. Gelman, R. A.; Poppke, D. C.; and Piez, K. A. Collagen fibril formation in vitro, *J. Biol. Chem.* 1979, 254, 11741-11754.

57. Lapiere, Ch. M.; and Nusgens, B. Polymerization of procollagen in vitro, *Biochem. Piophys. Acta*, 1974, 342, 237-246.

58. Miyahar, M.; Nigeha, F. K.; and Prockop, D. J. Formation of collagen fibrils in vitro by cleavage of precursors of type I collagen in vitro *J. Biol. Chem.*, 1982, 257, 8442-8448.

59. Miyahara, M.; Hayashi, K.; Berger, J.; Tanzawa, K.; Nijeha, F. K.; Trelstad, R. L.; and Prockop, D. J. formation collagen fibrils, *J. Biol. Chem.*, 1984, 259, 9891-9898.

60. Kadler, K. E.; Hojima, Y.; and Prockop, D. J. Assembly of collagen fibrils de novo by cleavage of the type I pC-collagen with procollagen C- proteinase, *J. Biol. Chem.*, 1987, 260, 32, 15696-15701.

61. Berg, R. A.; Birk, D. E; and Silver, F. H. Physical characterization of type I procollagen in solution: evidence that the properties limit self-assembly, *Int. J. Biol. Macromol.*, 1986, 8, 177-182.

62. Birk, D. E.; and Lande, M. A. Corneal and scleral collagen fiber formation in vitro, *Biochim. Biophys. Acta*, 1981, 670, 362-369.

63. Toole, B. P.; and Lowther, D. A. The effect of chondroitin sulfate-protein on the formation of collagen fibrils in vitro, *Biochem. J.*, 1968, 109, 857-866.

64. Snowden, J. M.; and Swann, D. A. The formation and thermal stability of in vitro assembled fibrils from acid-soluble and pepsin-treated collagens, *Biochem. Biophys. Acta*, 1979, 580, 372.

65. Kleinman, H. K.; Wilkes, M.; and Martin, G. R. Interaction of fibronectin with collagen fibrils, Biochemistry, 1981, 20 2325-2330.

66. Vogel, K. G.; Paulsson, M.; and Heinegard, D.— Specific inhibition of type I and type II collagen fibrillogenesis by the small proteoglycan of tendon, *Biochem. J.*, 1984, 233, 587-597.

67. Chandraskekhar, S.; Kleinman, H. K.; Hassel, J. R.; Martin, G. R.; Termin, J. D.; and Trelstad, R. L. Regulation of type I collagen fibril assembly by link protein and proteoglycans, *Collagen Rel. Res.*, 1984, 4, 232.

68. Farber, S.; Garg, A. K.; Birk, D. E.; and Silver, F. H. Collagen fibrillogenesis in vitro: evidence for prenucleation and nucleation steps, *Int. J. Biol. Macromol.*, 1986, 8, 37–42.
69. Brokaw, J. L.; Doillon, C. J.; Hahn, R. A.; Birk, D. E.; Berg, R. A.; and Silver, F. H. Turbidimetric and morphological studies of type I collagen fiber self assembly in vitro and the influence of fibronectin, *Int. J. Biol. Macromol.*, 1985, 7, 135–140.
70. Silver, F. H.; and Birk, D. E. Kinetic analysis of collagen fibrillogenesis: I. use of turbidity-time data, *Collagen Rel. Res.*, 1983, 3, 393–405.
71. Lowther D. A.; and Natarajan M. The influence of glycoprotein on collagen fibril formation in the presence of chondroitin sulfate proteoglycan, *Biochem J.*, 1972, 127, 607–608.
72. Uldberg, N.; and Danielsen, C. C. A study of the interaction in vitro between type I collagen and a small dermatan sulfate proteoglycan, *Biochem. J.*, 1988, 251, 643–648.
73. Silver, F. H.; and Trelstad, R. L. Type Collagen in Solution, *J. Biol. Chem.*, 1981, 255, 9427–9433.
74. Wood, G. C.; and Keech M. K. The formation of fibrils from collagen solutions. The effect of experimental conditions: kinetics and electron microscopic studes, *Biochem. J.*, 1960, 75, 588–598.
75. Obrink B. A study of the interactions between monomeric tro-pocollagen and glycosaminoglycans, *Eur. J. Biochem.*, 1973, 33, 387–400.
76. Swann, D. A.; Garg, H. G.; Jung, W.; and Hermann, H., Studies on human scar tissue proteoglycans, *J. Invest. Dermat.*, 1985, 84, 527–531.
77. Swann, D. A.; Powell, S.; and Sotman, S. The Heterogeneity of cartilage proteoglycans, *J. Biol. Chem.*, 1979 254 (3), 945–954. 78.
78. Sato, H.; Ellis, G. W.; and Inoue, S. Microtubular origin of mitotic spindle form birefringence, *J. Cell Biology*, 1975, 67, 501–517.
79. Davidson, E. A. Analysis of sugars found in mucopolysaccharides in *Methods in Enzymology*, vol 8, (Colowick, S. P. and Kaplan, M. O., editors), Academic Press, New York, NY pp. 52–55, 1966.
80. Scott, J. E.; and Haigh, M., Proteoglycan - type I collagen fibril interactions in bone and non-calcifying connective tissues, *Bioscience Reports*, 1985, 5, 71–81. 81.
81. Dunn, M. G.; Silver, F. H.; and Swann, D. A., Mechanical analysis of hypertrophic scar tissue: structural basis for apparent increased rigidity, *J. Invest. Dermat.*, 1985, 84, 9–13.
82. Silver, F. H.; Doillon, C. J., Introduction to the Study of Connective Tissues, *Biocompatible interactive implantable and biological materials*, vol. 1 (1989) in press VCH Publishers, New York, NY.

What is claimed is:

1. A biocompatible, biodegradable graft which is a tendon of improved mechanical properties which comprises aligned cross-linked synthetic collagen fibers embedded in a non-crosslinked and loose collagen matrix, said fibers having a diameter in the range of 20 to about 60 microns.

2. The biocompatible, biodegradable graft of claim 1, wherein said fibers have a diameter in the range of 20 to about 60 microns.

3. The biocompatible, biodegradable graft of claim 2 which is elastic.

4. The biocompatible, biodegradable graft of claim 3 which maintains elongation of 15 percent to failure.

5. The biocompatible, biodegradable graft of claim 3 of improved ultimate tensile strength (UTS) which comprises proteoglycans wherein the protoglycans have an average molecular weight of at least 500,000, wherein the protoglycans are incorporated into the interfibrillar spaces.

6. The biocompatible, biodegradable graft of claim 5 wherein the content of proteoglycans does not exceed about one percent by weight.

7. The biocompatible, biodegradable graft of claim 6 wherein the proteoglycans have a molecular weight in the range of about 1,000,000 to about 3,000,000.

8. The biocompatible, biodegradable graft of claim 7 which has an UTS in excess of 30 MPA.

9. The biocompatible, biodegradable graft of claim 8 which has an UTS in the range of about 30 to about 130 MPA.

10. The biocompatible, biodegradable graft of claim 9 which has an UTS in the range of about 70 to about 120 MPA.

11. The biocompatible, biodegradable graft of claim 8 which has a wet ultimate strain in the range of about $17.50 \pm 4.40$, $14.70 \pm 2.10$ and $17.70 \pm 2.20$ at strain rates of 10, 50 and 100 percent, respectively.

12. The biocompatible, biodegradable graft of claim 9 which has wet low strain modules in the range of about $179.5 \pm 54.7$, $198.1 \pm 56.7$ and $170.1 \pm 32.9$ at strain rates of 10, 50 and 100 percent, respectively.

13. The biocompatible, biodegradable graft of claim 8 which has a wet ultimate strain in the range of about $16.10 \pm 2.70$, $13.0 \pm 2.90$ and $14.50 \pm 3.50$ at strain rates of 10, 50 and 100 percent, respectively, wherein the fibres were 2 days cross-linked fibers.

14. The biocompatible, biodegradable graft of claim 8 which has wet low strain modules in the range of about $407.0 \pm 96.6$, $503.0 \pm 127.7$ and $412.0 \pm 83.4$ at strain rates of 10, 50 and 100 percent, respectively, wherein the fibers were 2 days cross-linked fibers.

15. The biocompatible, biodegradable graft of claim 8 which has an UTS in the range of about $27.4 \pm 5.60$, $23.9 \pm 3.80$ and $31.3 \pm 4.70$ at strain rates of 10, 50 and 100 percent, respectively.

16. The biocompatible, biodegradable graft of claim 8 which has an UTS in the range of about $66.2 \pm 17.20$, $59.2 \pm 17.30$ and $50.0 \pm 17.40$ at strain rates of 10, 50 and 100 percent, respectively, with 2 days cross-linked fibers.

17. The biocompatible, biodegradable graft of claim 10 wherein the graft is selected from the group consisting of a sheet, a tube, a mesh, a film, a filament, a fiber and a woven or non-woven sheet.

18. The biocompatible, biodegradable graft of claim 10 which has an UTS which is in excess of an autograph or of naturally occurring tendon fibers of rats.

* * * * *